US011229699B2

(12) United States Patent
Tarpey

(10) Patent No.: US 11,229,699 B2
(45) **Date of Patent: *Jan. 25, 2022**

(54) FELINE CALICIVIRUS VACCINE

(71) Applicant: Intervet Inc., Madison, NJ (US)

(72) Inventor: Ian Tarpey, St. Ives (GB)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/759,945

(22) PCT Filed: Nov. 5, 2018

(86) PCT No.: PCT/EP2018/080096

§ 371 (c)(1),
(2) Date: Apr. 28, 2020

(87) PCT Pub. No.: WO2019/110213

PCT Pub. Date: Jun. 13, 2019

(65) Prior Publication Data

US 2020/0338186 A1 Oct. 29, 2020

Related U.S. Application Data

(60) Provisional application No. 62/596,508, filed on Dec. 8, 2017, provisional application No. 62/582,050, filed on Nov. 6, 2017, provisional application No. 62/581,955, filed on Nov. 6, 2017, provisional application No. 62/599,401, filed on Dec. 15, 2017.

(51) Int. Cl.

| | |
|---|---|
| ***A61K 39/12*** | (2006.01) |
| ***C12N 7/00*** | (2006.01) |
| ***A61K 39/295*** | (2006.01) |
| ***A61K 39/118*** | (2006.01) |
| *A61K 39/00* | (2006.01) |

(52) U.S. Cl.

CPC .......... *A61K 39/295* (2013.01); *A61K 39/118* (2013.01); *A61K 39/12* (2013.01); *C12N 7/00* (2013.01); *A61K 2039/53* (2013.01); *A61K 2039/552* (2013.01); *A61K 2039/70* (2013.01); *C12N 2770/36143* (2013.01)

(58) Field of Classification Search

None

See application file for complete search history.

(56) References Cited

U.S. PATENT DOCUMENTS

| | | | | |
|---|---|---|---|---|
| 7,449,323 B2 | 11/2008 | Foley et al. | | |
| 8,460,913 B2 | 6/2013 | Kamrud et al. | | |
| 8,685,412 B2 * | 4/2014 | Huang | A61P 31/12 | 424/216.1 |
| 9,441,247 B2 | 9/2016 | Rayner et al. | | |
| 2013/0064839 A1 | 3/2013 | Harris et al. | | |
| 2015/0159143 A1 * | 6/2015 | Dowdy | C12N 5/0696 | 435/7.1 |
| 2015/0299728 A1 * | 10/2015 | Rayner | A61P 37/04 | 435/91.1 |

FOREIGN PATENT DOCUMENTS

| | | | |
|---|---|---|---|
| WO | 2001066568 A2 | | 9/2001 |
| WO | WO 2004/083390 | * | 9/2004 |
| WO | 2017109045 A1 | | 6/2017 |
| WO | WO 2017109045 | * | 6/2017 |

OTHER PUBLICATIONS

Alignment of SEQ ID 2 with Geneseq db access No. BEB26323 in WO 2017109045 Aug. 2017 by Shehu et al.*
Alignment of SEQ ID 4 with Geneseq db access No. BEB26324 in WO 2017109045 Jun. 2017 by Shehu et al.*
Carroll et al. (Vaccine. 2011; 29: 931-940).*
Arjona, Alvaro et al., Seroepidemiological Survey of Infection by Feline Leukemia Virus and Immunodeficiency Virus in Madrid and Correlation with Some Clinical Aspects, Journal of Clinical Microbiology, 2000, 3448-3449, 38.
Atkins, GJ et al, Therapeutic and prophylactic applications of alphavirus vectors, Expert Reviews in Molecular Medicine, 2008, e33, 1-18, 10(1).
Braley, Jo, FeLV and FIV: Survey Shows Prevalence in the United States and Europe, Feline Practice—Infectious Disease, 1994, 25-29, 22.
Bredenbeek, Peter J. et al., Sindbis Virus Expression Vectors: Packaging of RNA Replicons by Using Defective Helper RNAs, Journal of Virology, 1993, 6439-6446, 67(11).
De Noronha, F. et al., Influence of Antisera To Oncornavirus Glycoprotein (gp71) on Infections of Cats with Feline Leukemia Virus, Virology, 1978, 617-621, 85.
Flynn, J. Norman et al., Longitudinal Analysis of Feline Leukemia Virus-Specific Cytotoxic T Lymphocytes: Correlation with Recovery from Infection, Journal of Virology, 2002, 2306-2315, 76(5).
Grosenbaugh, Da et al, Comparison of the Safety and Efficacy of a Recombinant Feline Leukemia Virus (FeLV) Vaccine Delivered Transdermally and an Inactivated FeLV Vaccine Delivered Subcutaneously, Veterinary Therapeutics, Veterinary Learning Systems, 2004, 258-262, 5(4).
Hardy, Jr., William D. et al., Ten-year study comparing enzyme-linked immunosorbent assay with the immunofluorescent antibody test for detection of feline leukemia virus infection in cats, JAVMA, 1991, 1365-1373, 199 (10).
Hines, David L. et al., Evaluation of efficacy and safety of an inactivated virus vaccine against feline leukemia virus infection, J. Am. Vet. Med. Assoc., 1991, 1428-1430, 199.
Hoover, Edward A. et al., Feline leukemia virus infection and diseases, J. Am. Vet. Med. Assoc., 1991, 1287-1297, 199.
Hosie, M.J. et al., Prevalence of feline leukaemia virus and antibodies to feline immunodeficiency virus in cats in the United Kingdom, Veterinary Records, 1989, 293-297, 128.
International Search Report for PCT/EP2018080096 dated Feb. 19, 2019, 18 pages.

(Continued)

*Primary Examiner* — Shanon A. Foley
(74) *Attorney, Agent, or Firm* — Michael D. Davis

(57) ABSTRACT

The present invention provides new feline calicivirus vaccines, including multivalent vaccines. The present invention also provides methods of making and using the vaccines.

20 Claims, No Drawings

Specification includes a Sequence Listing.

(56) References Cited

OTHER PUBLICATIONS

Kamrud, K.I. et al., Development and characterization of promoter-less helper RNAs for the production of alphavirus replicon particle, Journal of General Virology, 2010, 1723-1727, 91(Pt 7).
Kass, P et al, Epidemiologic evidence for a causal relation between vaccination and fibrosarcoma tumorigenesis in cats, Journal of the American Veterinary Medical Association, 1993, 396-405, 203(3).
Konopka, Jennifer L. et al., Acute Infection with Venezuelan Equine Encephalitis Virus Replicon Particles Catalyzes a Systemic Antiviral State and Protects from Lethal Virus Challenge, Journal of Virology, 2009, 12432-12442, 83(29).
Levy, Julie et al., 2008 American Association of Feline Practitioners' feline retrovirus management guidelines, Journal of Feline Medicine and Surgery, 2008, 300-316, 10.
Liljestrom, P. et al., A new generation of animal cell expression vectors based on the semliki forest virus replicon, Biotechnology, 1991, pp. 1356-1361, 9.
Liu, Chunguo et al., Complete Genome Sequence of Feline Panleukopenia Virus Strain HRB-CS1, Isolated from a Domestic Cat in Northeastern China, Genome Announcements, 2015, 1, 3(2):e01556-14.
Ljungberg, K et al, Self-replicating alphavirus RNA vaccines, Expert Review of Vaccines, 2015, 177-194, 14(2).
Lucchese, G et al, How a single amino acid change may alter the immunological information of a peptide, Frontiers in Bioscience: Elite Edition, 2012, 1843-1852, vol. 4, No. 5.
Malik, R. et al., Prevalences of feline leukaemia virus and feline immunodeficiency virus infections in cats in Sydney, Australian Veterinary Journal, 1997, 323-327, 75.
Mathes L.E. et al., Abrogation of lymphocyte blastogenesis by a feline leukaemia virus protein, Nature, 1978, 687-689, 274.
Nunberg, J.H. et al., Method to map antigenic determinants recognized by monoclonal antibodies: Localization of a determinant of virus neutralization on the feline leukemia virus envelope protein gp7O, Proc. Natl. Acad. Sci. USA, 1984, 3675-3679, 81.
Pacitti, A.M. et al., Transmission of feline leukaemia virus in the milk of a non-viraemic cat, The Veterinary Record, 1986, 381-384, 118.
Patel, M et al, Comparative Efficacy of Feline Leukemia Virus (FeLV) Inactivated Whole-Virus Vaccine and Canarypox Virus-Vectored Vaccine during Virulent FeLV Challenge and Immunosuppression, Abstract, Clinical and Vaccine Immunology, 2015, 798-805, 22(7).
Pedersen, Niels C., Immunogenicity and Efficacy of a Commercial Feline Leukemia Virus Vaccine, J. Vet. Intern. Med., 1993, 34-39, 7.
Pushko, Peter et al., Replicon-Helper Systems from Attenuated Venezuelan Equine Encephalitis Virus: Expression of Heterologous Genes in Vitro and Immunization against Heterologous Pathogens in Vivo, Virology, 1997, 389-401, 239.
Radford, Alan D. et al., Feline calicivirus. Vet. Res., 2007, 319-335, 38(2).
Rayner, Jo et al., Alphavirus vectors and vaccination, Reviews in Medical Virology, 2002, pp. 279-296, 12.
Reed, DS et al, Combined Alphavirus Replicon Particle Vaccine Induces Durable and Cross-Protective Immune Responses against Equine Encephalitis Viruses, Journal of Virology, 2014, 12077-12086, vol. 88, No. 20.
Rojko, Jennifer L. et al., Pathogenesis of infection by the feline leukemia virus, J Am Vet Med Assoc, 1991, 1305-1310, 199.
Scherk, M.A., et al., 2013 AAFP Feline Vaccination Advisory Panel Report, Journal of Feline Medicine and Surgery, 2013, pp. 785-808, 15.
Scott, Fred W et al., Long-term immunity in cats vaccinated with an inactivated trivalent vaccine, Am. J. Vet. Res., 1999, 652-658, 60.
Segundo, Fayna Diaz-San et al., Venezuelan Equine Encephalitis Replicon Particles Can Induce Rapid Protection against Foot-and-Mouth Disease Virus, Journal of Virology, 2013, 5447-5460, 87(10).
Sosnovtsev, Stanislav V. et al., Identification and Genomic Mapping of the ORF3 and VPg Proteins in Feline Calicivirus Virions, Virology, 2000, 193-203, 277.
Sparkes, A.H., Feline leukaentia virus: a revie-w of immunity and vaccination, Journal of Small Animal Practice, 1997, 187-194, 38.
Stuke, K et al, Efficacy of an inactivated FeLV vaccine compared to a recombinant FeLV vaccine in minimum age cats following virulent FeLV challenge, Vaccine, 2014, 2599-2603, 32(22).
Thomsen, Darrell R. et al., Expression of feline leukaemia virus gp85 and gag proteins and assembly into virus-like particles using the baculovirus expression vector system, Journal of General Virology, 1992, 1819-1824, 73.
Torres, Andrea N. et al., Feline leukemia virus immunity induced by whole inactivated virus vaccination, Veterinary Immunology and Immunopathology, 2010, 122-131, 134.
Uematus, Y et al, Lack of Interference with Immunogenicity of a Chimeric Alphavirus Replicon Particle-Based Influenza Vaccine by Preexisting Antivector Immunity, Clinical and Vaccine Immunology, 2012, 991-998, vol. 19, No. 7.
Vander Veen, RL et al, Alphavirus replicon vaccines, Animal Health Research Reviews, 2012, 1-9, vol. 13, No. 1.

* cited by examiner

SEQUENCE LISTING

```
<160> NUMBER OF SEQ ID NOS: 16

<210> SEQ ID NO 1
<211> LENGTH: 1638
<212> TYPE: DNA
<213> ORGANISM: Artificial Sequence
<220> FEATURE:
<223> OTHER INFORMATION: codon optimized for feline

<400> SEQUENCE: 1

atggctgacg acggatctgt gaccacccca gaacaaggaa caatggtcgg aggagtgatt      60

gccgaaccca gcgctcagat gtcaactgcg gcggacatgg cctccggaaa gtcggtggac     120

tccgagtggg aagccttctt ctcgttccac acgtccgtga actggagcac ctccgaaacc     180

caaggaaaga tcctcttcaa gcagtccctg ggtcccctgc tgaacccgta cctggagcac     240

atcagcaagc tgtacgtcgc ttggagcggg tcgatcgaag tgcgattttc catctcggga     300

agcggcgtgt tcggtggtaa actggccgcc atcgtcgtgc cgcctggtgt cgaccctgtc     360

cagtcaacct ccatgctgca gtacccgcac gtcctgttcg acgcaagaca agtggagcca     420

gtgatcttct ccatcccgga cctccgcaac agcctgtatc acttgatgtc cgataccgat     480

accacttccc tcgtgatcat ggtgtacaac gatctgatca acccgtacgc caatgactcc     540

aacagctcgg gttgcatcgt gaccgtcgaa acgaagcctg gcatcgattt caagtttcat     600

ctgctgaaac cgcccggatc catgcttact cacgggtcca tcccttccga tctgatcccc     660

aagagctcct ccctgtggat tgggaaccgc cactggaccg atattaccga tttcgtgatt     720

cggcctttcg tgttccaagc caaccggcac ttcgacttca accaggagac tgccggctgg     780

tcaactccac ggttccgccc attggccgtg actgtgtcgc agtcaaaggg agccaagctc     840

gggaacggca tcgccaccga ctacattgtg cctggaatcc ccgacggatg gcctgatact     900

accatcccca ccaagctgac ccctaccgga gattacgcca tcacctcctc cgacggcaat     960

gatattgaaa ccaagctgga atacgagaac gcggacgtga ttaagaacaa caccaacttc    1020

cgctccatgt atatctgcgg aagcctccag agggcttggg gcgacaagaa gatcagcaac    1080

accgggttca tcactaccgg agtgatttct gacaactcca tcagcccttc gaacacaatt    1140

gaccagtcca agatcgtggt gtaccaggac aaccatgtca attcggaggt ccagactagc    1200
```

-continued

```
gacatcactc ttgccatcct gggctacacc ggaattggag aagaggccat aggcgccaac   1260

cgggactccg tcgtgagaat ttccgtgctt ccggaaactg gagcaagggg cggaaatcac   1320

cccatcttct acaaaaattc catgaagctg ggctacgtga tctcctccat tgacgtgttc   1380

aactcccaaa tcctccacac ctcgcgccag ctgtcactga acaactactt gttgcccccct   1440

gactccttcg cggtgtaccg gattattgac agcaacggat catggttcga cattgggatt   1500

gacagcgatg ggttttcatt cgtgggcgtg tcgtcatttc caaagctgga gtttccgctg   1560

tccgcctcat acatgggcat ccagctcgca aagatccggc tggcgtccaa catccggtca   1620

tccatgacta agctgtga                                                 1638


<210> SEQ ID NO 2
<211> LENGTH: 545
<212> TYPE: PRT
<213> ORGANISM: Feline calicivirus

<400> SEQUENCE: 2

Met Ala Asp Asp Gly Ser Val Thr Thr Pro Glu Gln Gly Thr Met Val
1               5                   10                  15

Gly Gly Val Ile Ala Glu Pro Ser Ala Gln Met Ser Thr Ala Ala Asp
            20                  25                  30

Met Ala Ser Gly Lys Ser Val Asp Ser Glu Trp Glu Ala Phe Phe Ser
        35                  40                  45

Phe His Thr Ser Val Asn Trp Ser Thr Ser Glu Thr Gln Gly Lys Ile
    50                  55                  60

Leu Phe Lys Gln Ser Leu Gly Pro Leu Leu Asn Pro Tyr Leu Glu His
65                  70                  75                  80

Ile Ser Lys Leu Tyr Val Ala Trp Ser Gly Ser Ile Glu Val Arg Phe
                85                  90                  95

Ser Ile Ser Gly Ser Gly Val Phe Gly Gly Lys Leu Ala Ala Ile Val
            100                 105                 110

Val Pro Pro Gly Val Asp Pro Val Gln Ser Thr Ser Met Leu Gln Tyr
        115                 120                 125

Pro His Val Leu Phe Asp Ala Arg Gln Val Glu Pro Val Ile Phe Ser
    130                 135                 140

Ile Pro Asp Leu Arg Asn Ser Leu Tyr His Leu Met Ser Asp Thr Asp
145                 150                 155                 160

Thr Thr Ser Leu Val Ile Met Val Tyr Asn Asp Leu Ile Asn Pro Tyr
                165                 170                 175

Ala Asn Asp Ser Asn Ser Ser Gly Cys Ile Val Thr Val Glu Thr Lys
            180                 185                 190

Pro Gly Ile Asp Phe Lys Phe His Leu Leu Lys Pro Pro Gly Ser Met
        195                 200                 205

Leu Thr His Gly Ser Ile Pro Ser Asp Leu Ile Pro Lys Ser Ser Ser
    210                 215                 220

Leu Trp Ile Gly Asn Arg His Trp Thr Asp Ile Thr Asp Phe Val Ile
225                 230                 235                 240

Arg Pro Phe Val Phe Gln Ala Asn Arg His Phe Asp Phe Asn Gln Glu
                245                 250                 255

Thr Ala Gly Trp Ser Thr Pro Arg Phe Arg Pro Leu Ala Val Thr Val
            260                 265                 270

Ser Gln Ser Lys Gly Ala Lys Leu Gly Asn Gly Ile Ala Thr Asp Tyr
        275                 280                 285
```

```
Ile Val Pro Gly Ile Pro Asp Gly Trp Pro Asp Thr Thr Ile Pro Thr
    290                 295                 300

Lys Leu Thr Pro Thr Gly Asp Tyr Ala Ile Thr Ser Ser Asp Gly Asn
305                 310                 315                 320

Asp Ile Glu Thr Lys Leu Glu Tyr Glu Asn Ala Asp Val Ile Lys Asn
                325                 330                 335

Asn Thr Asn Phe Arg Ser Met Tyr Ile Cys Gly Ser Leu Gln Arg Ala
            340                 345                 350

Trp Gly Asp Lys Lys Ile Ser Asn Thr Gly Phe Ile Thr Thr Gly Val
        355                 360                 365

Ile Ser Asp Asn Ser Ile Ser Pro Ser Asn Thr Ile Asp Gln Ser Lys
    370                 375                 380

Ile Val Val Tyr Gln Asp Asn His Val Asn Ser Glu Val Gln Thr Ser
385                 390                 395                 400

Asp Ile Thr Leu Ala Ile Leu Gly Tyr Thr Gly Ile Gly Glu Glu Ala
                405                 410                 415

Ile Gly Ala Asn Arg Asp Ser Val Val Arg Ile Ser Val Leu Pro Glu
            420                 425                 430

Thr Gly Ala Arg Gly Gly Asn His Pro Ile Phe Tyr Lys Asn Ser Met
        435                 440                 445

Lys Leu Gly Tyr Val Ile Ser Ser Ile Asp Val Phe Asn Ser Gln Ile
    450                 455                 460

Leu His Thr Ser Arg Gln Leu Ser Leu Asn Asn Tyr Leu Leu Pro Pro
465                 470                 475                 480

Asp Ser Phe Ala Val Tyr Arg Ile Ile Asp Ser Asn Gly Ser Trp Phe
                485                 490                 495

Asp Ile Gly Ile Asp Ser Asp Gly Phe Ser Phe Val Gly Val Ser Ser
            500                 505                 510

Phe Pro Lys Leu Glu Phe Pro Leu Ser Ala Ser Tyr Met Gly Ile Gln
        515                 520                 525

Leu Ala Lys Ile Arg Leu Ala Ser Asn Ile Arg Ser Ser Met Thr Lys
    530                 535                 540

Leu
545


<210> SEQ ID NO 3
<211> LENGTH: 1629
<212> TYPE: DNA
<213> ORGANISM: Artificial Sequence
<220> FEATURE:
<223> OTHER INFORMATION: codon optimized for feline

<400> SEQUENCE: 3

atgactgccc cggaacaagg aacgatggtc ggaggagtga ttgcagaacc gtcagcacag      60

atgtccaccg ctgccgacat ggccactgga aagagcgtgg actccgaatg ggaagccttc     120

ttctccttcc acacttcggt caactggtcg actagcgaaa cccaggggaa gattttgttc     180

aagcaatccc tcggccctct gctgaacccc tacctggagc atctggccaa gctgtacgtg     240

gcatggtcgg gcagcatcga agtgcgcttt agcatttccg gctccggagt gttcgggga      300

aagcttgctg ccattgtcgt gccgccagga gtggacccgg tgcagtccac ttctatgctc     360

caatacccgc atgtcctgtt cgacgccaga caggtggagc ctgtgatctt ttgcctgccg     420

gatctcaggt ccaccctgta tcacctcatg tccgacaccg acaccacctc gctcgtgatc     480

atggtgtaca acgacctgat caaccccctac gctaacgacg ccaacagctc aggttgcatt    540
```

-continued

```
gtgactgtcg aaaccaagcc aggccctgac ttcaagtttc atttgctgaa gccgcccggt    600

tccatgctga cccacggctc gatcccatcc gacctgatcc ccaagacgag ctccctgtgg    660

atcggaaacc gctactggtc cgatattacc gacttcgtga tcagaccatt cgtgttccaa    720

gccaaccgcc atttcgactt caaccaggaa accgcaggat ggtcgacccc tcgattccgc    780

ccgatttcag tgaccatcac cgaacagaac ggcgcgaagc tgggaattgg cgtggcgacc    840

gactacatcg tgccgggaat cccggatgga tggcctgata cgaccattcc cggggagctg    900

atccctgccg gggactacgc catcaccaac ggtactggaa acgacatcac cactgccacc    960

ggttacgaca ccgccgacat cataaagaac aacaccaact tcagaggaat gtacatttgc   1020

ggctccctgc aacgcgcttg ggtgacaaa aagatctcga acactgcctt catcacaaca   1080

gcgactctgg acggcgataa caacaacaag atcaatcctt gtaataccat cgaccagtcc   1140

aaaatcgtgg tgttccagga taaccacgtg ggaaagaagg cgcagacctc cgacgacact   1200

ctggcgctgc ttggctacac cgggatcggc gagcaggcca ttggaagcga tcgggatcgg   1260

gtcgtgcgga tctccaccct ccccgagact ggagcaaggg gaggcaacca ccccatcttt   1320

tacaaaaaca gcattaagct cggatacgtc atccgctcca tcgatgtgtt caactctcaa   1380

atcctgcaca cttcgcggca gctgtccctg aaccactacc tcttgccgcc cgactccttc   1440

gccgtctacc ggatcattga ttcgaacggg agctggttcg acatcggcat tgatagcgat   1500

ggcttctcgt ttgtgggcgt gtcgggcttc gggaagctgg agttcccact gagcgcctca   1560

tacatgggta tccagctggc caagatcagg ctggcctcca acatccgctc acctatgact   1620

aagctgtga                                                           1629


<210> SEQ ID NO 4
<211> LENGTH: 542
<212> TYPE: PRT
<213> ORGANISM: Feline calicivirus

<400> SEQUENCE: 4

Met Thr Ala Pro Glu Gln Gly Thr Met Val Gly Gly Val Ile Ala Glu
1               5                   10                  15

Pro Ser Ala Gln Met Ser Thr Ala Ala Asp Met Ala Thr Gly Lys Ser
            20                  25                  30

Val Asp Ser Glu Trp Glu Ala Phe Phe Ser Phe His Thr Ser Val Asn
        35                  40                  45

Trp Ser Thr Ser Glu Thr Gln Gly Lys Ile Leu Phe Lys Gln Ser Leu
    50                  55                  60

Gly Pro Leu Leu Asn Pro Tyr Leu Glu His Leu Ala Lys Leu Tyr Val
65                  70                  75                  80

Ala Trp Ser Gly Ser Ile Glu Val Arg Phe Ser Ile Ser Gly Ser Gly
                85                  90                  95

Val Phe Gly Gly Lys Leu Ala Ala Ile Val Val Pro Pro Gly Val Asp
            100                 105                 110

Pro Val Gln Ser Thr Ser Met Leu Gln Tyr Pro His Val Leu Phe Asp
        115                 120                 125

Ala Arg Gln Val Glu Pro Val Ile Phe Cys Leu Pro Asp Leu Arg Ser
    130                 135                 140

Thr Leu Tyr His Leu Met Ser Asp Thr Asp Thr Thr Ser Leu Val Ile
145                 150                 155                 160

Met Val Tyr Asn Asp Leu Ile Asn Pro Tyr Ala Asn Asp Ala Asn Ser
                165                 170                 175
```

-continued

```
Ser Gly Cys Ile Val Thr Val Glu Thr Lys Pro Gly Pro Asp Phe Lys
            180                 185                 190

Phe His Leu Leu Lys Pro Pro Gly Ser Met Leu Thr His Gly Ser Ile
        195                 200                 205

Pro Ser Asp Leu Ile Pro Lys Thr Ser Ser Leu Trp Ile Gly Asn Arg
    210                 215                 220

Tyr Trp Ser Asp Ile Thr Asp Phe Val Ile Arg Pro Phe Val Phe Gln
225                 230                 235                 240

Ala Asn Arg His Phe Asp Phe Asn Gln Glu Thr Ala Gly Trp Ser Thr
                245                 250                 255

Pro Arg Phe Arg Pro Ile Ser Val Thr Ile Thr Glu Gln Asn Gly Ala
            260                 265                 270

Lys Leu Gly Ile Gly Val Ala Thr Asp Tyr Ile Val Pro Gly Ile Pro
        275                 280                 285

Asp Gly Trp Pro Asp Thr Thr Ile Pro Gly Glu Leu Ile Pro Ala Gly
    290                 295                 300

Asp Tyr Ala Ile Thr Asn Gly Thr Gly Asn Asp Ile Thr Thr Ala Thr
305                 310                 315                 320

Gly Tyr Asp Thr Ala Asp Ile Ile Lys Asn Asn Thr Asn Phe Arg Gly
                325                 330                 335

Met Tyr Ile Cys Gly Ser Leu Gln Arg Ala Trp Gly Asp Lys Lys Ile
            340                 345                 350

Ser Asn Thr Ala Phe Ile Thr Thr Ala Thr Leu Asp Gly Asp Asn Asn
        355                 360                 365

Asn Lys Ile Asn Pro Cys Asn Thr Ile Asp Gln Ser Lys Ile Val Val
    370                 375                 380

Phe Gln Asp Asn His Val Gly Lys Lys Ala Gln Thr Ser Asp Asp Thr
385                 390                 395                 400

Leu Ala Leu Leu Gly Tyr Thr Gly Ile Gly Glu Gln Ala Ile Gly Ser
                405                 410                 415

Asp Arg Asp Arg Val Val Arg Ile Ser Thr Leu Pro Glu Thr Gly Ala
            420                 425                 430

Arg Gly Gly Asn His Pro Ile Phe Tyr Lys Asn Ser Ile Lys Leu Gly
        435                 440                 445

Tyr Val Ile Arg Ser Ile Asp Val Phe Asn Ser Gln Ile Leu His Thr
    450                 455                 460

Ser Arg Gln Leu Ser Leu Asn His Tyr Leu Leu Pro Pro Asp Ser Phe
465                 470                 475                 480

Ala Val Tyr Arg Ile Ile Asp Ser Asn Gly Ser Trp Phe Asp Ile Gly
                485                 490                 495

Ile Asp Ser Asp Gly Phe Ser Phe Val Gly Val Ser Gly Phe Gly Lys
            500                 505                 510

Leu Glu Phe Pro Leu Ser Ala Ser Tyr Met Gly Ile Gln Leu Ala Lys
        515                 520                 525

Ile Arg Leu Ala Ser Asn Ile Arg Ser Pro Met Thr Lys Leu
    530                 535                 540
```

<210> SEQ ID NO 5
<211> LENGTH: 1929
<212> TYPE: DNA
<213> ORGANISM: Artificial Sequence
<220> FEATURE:
<223> OTHER INFORMATION: codon optimized for feline

<400> SEQUENCE: 5
atggagtcac caacacaccc taaaccttct aaagacaaaa ccctctcgtg gaatctcgcc 60
ttccttgtgg gcatcctgtt cacaatcgac atcggcatgg ccaacccttc gccgcatcag 120
atctacaatg tgacatgggt cattactaat gtgcagacaa acacccaggc aaatgctact 180
tctatgcttg gtactctgac tgatgcttat ccaaccctgc acgtcgacct ttgcgatctc 240
gtcggtgaca catgggagcc catcgtgctg aatccaacta atgtcaaaca tggtgccagg 300
tattcttcta gcaaatacgg gtgtaagacc actgatcgga agaaacagca acaaacctac 360
ccattctacg tgtgcccggg tcacgcaccg tccctgggtc cgaagggaac acattgtggg 420
ggagcccaag acggtttttg cgctgcttgg ggttgtgaaa caaccggaga agcctggtgg 480
aagcctacct catcttggga ctacattact gtgaaaagag gctctagcca ggataacagc 540
tgcgaaggaa agtgtaatcc cctggtgctt caattcaccc agaaaggccg gcaggcatca 600
tgggatggac cgaaaatgtg gggacttaga ctctatcgca ccggatacga ccccatcgct 660
ctgtttactg tgtcacgcca agtctccacc attactccgc cacaggccat ggggccgaat 720
ctggtcctcc ccgatcagaa gccaccctca cggcaaagtc aaaccggctc aaaagtggcc 780
acccaacggc cccagacaaa tgagtccgca cctaggtcag tggcacctac aacaatgggt 840
ccaaagcgga tcggaaccgg agacaggctc attaacctcg tgcaagggac ttatctggcc 900
cttaacgcta ctgaccccaa caagaccaag gattgctggc tctgccttgt gagcagacct 960
ccttactatg aggggatcgc cattctcgga aactactcaa atcagaccaa ccccccctccg 1020
tcgtgtctga gcacccccca gcacaagctt actatttcag aagtcagtgg acagggaatg 1080
tgcatcggaa ccgtgccaaa gactcatcaa gccctttgca acaaaactca acaagggcac 1140
actggagctc attatctcgc cgcacctaac gggacctact gggcttgcaa tactggattg 1200
accccgtgta tctctatggc cgtgctgaat tggacttccg acttctgcgt gcttattgag 1260
ctttggccta gagtgacata ccatcagcct gagtacgtct atacccattt cgccaaggca 1320
gtcagattcc ggcgggagcc tatctccctg actgtggcct tgatgctcgg tggactgaca 1380
gtgggaggaa ttgcagctgg agtcggaact ggaaccaagg ccctgctcga aactgctcag 1440
ttccggcagc tgcagatggc catgcacact gacatccagg ctctggagga atcaatttca 1500
gcccttgaga aaagcttgac ctcgctgtct gaagtggtcc tccaaaacag gcgcggtttg 1560
gacatcctgt tccttcaaga gggtggtctg tgcgccgctc tcaaggagga atgctgtttc 1620
tacgctgacc ataccgggct ggtgcgcgat aacatggcaa agctgcggga acgcttgaaa 1680
cagaggcagc aactgttcga ctctcagcag ggatggttcg agggctggtt taacaagagc 1740
ccatggttta ccactctgat ctcttcaatc atgggtccac tgctcatcct gcttctgatt 1800
cttctcttcg gaccgtgtat tctcaacagg ctggtgcagt ttgtcaagga cagaatctcg 1860
gtggtccagg ccctgattct tactcagcag tatcagcaga ttaagcagta cgaccccgat 1920
cggccttga 1929

<210> SEQ ID NO 6
<211> LENGTH: 642
<212> TYPE: PRT
<213> ORGANISM: Feline leukemia virus

<400> SEQUENCE: 6

Met Glu Ser Pro Thr His Pro Lys Pro Ser Lys Asp Lys Thr Leu Ser
1 5 10 15

-continued

```
Trp Asn Leu Ala Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Met Cys Ile Gly Thr Val Pro Lys Thr
        355                 360                 365

His Gln Ala Leu Cys Asn Lys Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
            420                 425                 430
```

-continued

```
Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Lys Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro
```

<210> SEQ ID NO 7
<211> LENGTH: 1233
<212> TYPE: DNA
<213> ORGANISM: Artificial Sequence
<220> FEATURE:
<223> OTHER INFORMATION: codon optimized for feline

<400> SEQUENCE: 7

```
aatcctagtc cacaccaaat atataatgta acttgggtaa taaccaatgt acaaactaac      60

acccaagcta acgccacctc tatgttagga accttaaccg atgcctaccc taccctacat     120

gttgacttat gtgacctagt gggagacacc tgggaaccta tagtcctaaa cccaaccaat     180

gtaaaacacg gggcacgtta ctcctcctca aaatatggat gtaaaactac agatagaaaa     240

aaacagcaac agacataccc cttttacgtc tgccccggac atgccccctc gttggggcca     300

aagggaacac attgtggagg ggcacaagat gggttttgtg ccgcatgggg atgtgagacc     360

accggagaag cttggtggaa gcccacctcc tcatgggact atatcacagt aaaaagaggg     420

agtagtcagg acaatagctg tgagggaaaa tgcaaccccc tggttttgca gttcacccag     480

aagggaagac aagcctcttg ggacggacct aagatgtggg gattgcgact ataccgtaca     540

ggatatgacc ctatcgcttt attcacggtg tcccggcagg tatcaaccat tacgccgcct     600

caggcaatgg gaccaaacct agtcttacct gatcaaaaac ccccatcccg acaatctcaa     660

acagggtcca aagtggcgac ccagaggccc caaacgaatg aaagcgcccc aaggtctgtt     720

gcccccacca ccatgggtcc caaacggatt gggaccggag ataggttaat aaatttagta     780

caagggacat acctagcctt aaatgccacc gaccccaaca aaactaaaga ctgttggctc     840
```

```
tgcctggttt ctcgaccacc ctattacgaa gggattgcaa tcttaggtaa ctacagcaac    900

caaacaaacc cccccccatc ctgcctatct actccgcaac acaaactaac tatatctgaa    960

gtatcagggc aaggaatgtg catagggact gttcctaaaa cccaccaggc tttgtgcaat   1020

aagacacaac agggacatac aggggcgcac tatctagccg cccccaacgg cacctattgg   1080

gcctgtaaca ctggactcac ccatgcatt tccatggcgg tgctcaattg gacctctgat   1140

ttttgtgtct taatcgaatt atggcccaga gtgacttacc atcaacccga atatgtgtac   1200

acacattttg ccaaagctgt caggttccga aga                                1233


<210> SEQ ID NO 8
<211> LENGTH: 411
<212> TYPE: PRT
<213> ORGANISM: Feline leukemia virus

<400> SEQUENCE: 8

Asn Pro Ser Pro His Gln Ile Tyr Asn Val Thr Trp Val Ile Thr Asn
1               5                   10                  15

Val Gln Thr Asn Thr Gln Ala Asn Ala Thr Ser Met Leu Gly Thr Leu
            20                  25                  30

Thr Asp Ala Tyr Pro Thr Leu His Val Asp Leu Cys Asp Leu Val Gly
        35                  40                  45

Asp Thr Trp Glu Pro Ile Val Leu Asn Pro Thr Asn Val Lys His Gly
    50                  55                  60

Ala Arg Tyr Ser Ser Ser Lys Tyr Gly Cys Lys Thr Thr Asp Arg Lys
65                  70                  75                  80

Lys Gln Gln Gln Thr Tyr Pro Phe Tyr Val Cys Pro Gly His Ala Pro
                85                  90                  95

Ser Leu Gly Pro Lys Gly Thr His Cys Gly Gly Ala Gln Asp Gly Phe
            100                 105                 110

Cys Ala Ala Trp Gly Cys Glu Thr Thr Gly Glu Ala Trp Trp Lys Pro
        115                 120                 125

Thr Ser Ser Trp Asp Tyr Ile Thr Val Lys Arg Gly Ser Ser Gln Asp
    130                 135                 140

Asn Ser Cys Glu Gly Lys Cys Asn Pro Leu Val Leu Gln Phe Thr Gln
145                 150                 155                 160

Lys Gly Arg Gln Ala Ser Trp Asp Gly Pro Lys Met Trp Gly Leu Arg
                165                 170                 175

Leu Tyr Arg Thr Gly Tyr Asp Pro Ile Ala Leu Phe Thr Val Ser Arg
            180                 185                 190

Gln Val Ser Thr Ile Thr Pro Pro Gln Ala Met Gly Pro Asn Leu Val
        195                 200                 205

Leu Pro Asp Gln Lys Pro Pro Ser Arg Gln Ser Gln Thr Gly Ser Lys
    210                 215                 220

Val Ala Thr Gln Arg Pro Gln Thr Asn Glu Ser Ala Pro Arg Ser Val
225                 230                 235                 240

Ala Pro Thr Thr Met Gly Pro Lys Arg Ile Gly Thr Gly Asp Arg Leu
                245                 250                 255

Ile Asn Leu Val Gln Gly Thr Tyr Leu Ala Leu Asn Ala Thr Asp Pro
            260                 265                 270

Asn Lys Thr Lys Asp Cys Trp Leu Cys Leu Val Ser Arg Pro Pro Tyr
        275                 280                 285

Tyr Glu Gly Ile Ala Ile Leu Gly Asn Tyr Ser Asn Gln Thr Asn Pro
    290                 295                 300
```

```
Pro Pro Ser Cys Leu Ser Thr Pro Gln His Lys Leu Thr Ile Ser Glu
305                 310                 315                 320

Val Ser Gly Gln Gly Met Cys Ile Gly Thr Val Pro Lys Thr His Gln
                325                 330                 335

Ala Leu Cys Asn Lys Thr Gln Gln Gly His Thr Gly Ala His Tyr Leu
            340                 345                 350

Ala Ala Pro Asn Gly Thr Tyr Trp Ala Cys Asn Thr Gly Leu Thr Pro
        355                 360                 365

Cys Ile Ser Met Ala Val Leu Asn Trp Thr Ser Asp Phe Cys Val Leu
    370                 375                 380

Ile Glu Leu Trp Pro Arg Val Thr Tyr His Gln Pro Glu Tyr Val Tyr
385                 390                 395                 400

Thr His Phe Ala Lys Ala Val Arg Phe Arg Arg
                405                 410


<210> SEQ ID NO 9
<211> LENGTH: 1575
<212> TYPE: DNA
<213> ORGANISM: Artificial Sequence
<220> FEATURE:
<223> OTHER INFORMATION: codon optimized for human

<400> SEQUENCE: 9

atggtgccgc aggctctcct gtttgtcccc cttctggtct ttccattgtg ttttgggaaa     60

ttccctatct acacaattcc ggacaagttg ggaccctgga gcccaattga cattcatcat    120

ctcagctgcc cgaacaattt ggtcgtggag gacgaaggat gcaccaacct gtcggggttc    180

tcctacatgg aattgaaagt cggatacatc agtgccatta agatgaacgg gttcacttgc    240

acaggcgtcg tgactgaagc tgagacatac actaacttcg tgggatatgt cactaccact    300

ttcaaaagaa agcatttccg ccctactcct gatgcttgta gggccgcata caactggaag    360

atggccggtg accccagata tgaggaatca cttcacaatc cgtaccctga ctaccactgg    420

cttcggactg tcaaaaccac caaggagtca ctcgtgatca ttagtccaag tgtggctgat    480

cttgacccat acgaccggtc acttcactca cgggtgttcc cgggggggaa ttgctctggt    540

gtcgcagtgt cgtcaaccta ctgctccaca aaccacgatt acaccatttg gatgccagaa    600

aatcctcggc ttggtatgtc atgtgacatt ttcaccaatt ctcgggggaa gagggcttcc    660

aaagggtctg aaacttgcgg ctttgtcgat gagcggggct tgtataagtc acttaaaggt    720

gcttgcaaac tcaagctttg tggtgtcttg ggattgagat tgatggatgg aacttgggtc    780

gcaatgcaga cttctaacga aaccaaatgg tgccctcccg gacagcttgt gaatttgcat    840

gactttcgct ctgacgaaat tgagcatctt gtcgtcgagg agttggtcaa gaagcgggaa    900

gagtgtctgg atgctttgga atcaatcatg accaccaagt cagtgtcttt cagacggctc    960

tcacatctta ggaaattggt gccaggtttt ggaaaagcat ataccatttt caacaagacc   1020

cttatggaag ccgatgctca ctacaagtct gtcaggactt ggaatgagat catcccgtct   1080

aaagggtgtc ttagggtcgg agggagatgt catcctcatg tcaacggagt ctttttcaat   1140

ggtatcattc ttggacctga cggaaatgtc cttatccctg agatgcaatc ttccctcctc   1200

cagcaacaca tggaacttct tgtctcatcg gtcatccccc ttatgcaccc cctggctgac   1260

ccatcaaccg tgttcaagaa cggtgacgag gcagaggatt ttgtcgaggt ccaccttccc   1320

gatgtgcatg aacggatctc tggtgtcgac cttggactcc ctaactgggg aaagtatgtc   1380

cttctgtcgg caggagccct gactgccttg atgttgatta tcttcctgat gacttgttgg   1440
```

-continued aggagagtca atcggtcgga gccaacacaa cataatctca gaggaacagg aagggaggtg   1500
tcagtcacac cccaaagcgg gaagatcatt tcgtcttggg agtcatacaa gagcggaggt   1560
gaaaccggac tgtga                                                    1575

<210> SEQ ID NO 10
<211> LENGTH: 524
<212> TYPE: PRT
<213> ORGANISM: Rabies virus

<400> SEQUENCE: 10

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Gly Gly
                165                 170                 175

Asn Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Gly Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
355 360 365

Arg Cys His Pro His Val Asn Gly Val Phe Phe Asn Gly Ile Ile Leu
370 375 380

Gly Pro Asp Gly Asn Val Leu Ile Pro Glu Met Gln Ser Ser Leu Leu
385 390 395 400

Gln Gln His Met Glu Leu Leu Val Ser Ser Val Ile Pro Leu Met His
405 410 415

Pro Leu Ala Asp Pro Ser Thr Val Phe Lys Asn Gly Asp Glu Ala Glu
420 425 430

Asp Phe Val Glu Val His Leu Pro Asp Val His Glu Arg Ile Ser Gly
435 440 445

Val Asp Leu Gly Leu Pro Asn Trp Gly Lys Tyr Val Leu Leu Ser Ala
450 455 460

Gly Ala Leu Thr Ala Leu Met Leu Ile Ile Phe Leu Met Thr Cys Trp
465 470 475 480

Arg Arg Val Asn Arg Ser Glu Pro Thr Gln His Asn Leu Arg Gly Thr
485 490 495

Gly Arg Glu Val Ser Val Thr Pro Gln Ser Gly Lys Ile Ile Ser Ser
500 505 510

Trp Glu Ser Tyr Lys Ser Gly Gly Glu Thr Gly Leu
515 520

<210> SEQ ID NO 11
<211> LENGTH: 13
<212> TYPE: DNA
<213> ORGANISM: Artificial Sequence
<220> FEATURE:
<223> OTHER INFORMATION: 5 'flanking sequence

<400> SEQUENCE: 11
ggcgcgccgc acc 13

<210> SEQ ID NO 12
<211> LENGTH: 1638
<212> TYPE: RNA
<213> ORGANISM: Artificial Sequence
<220> FEATURE:
<223> OTHER INFORMATION: codon optimized for feline

<400> SEQUENCE: 12
auggcugacg acggaucugu gaccacccca gaacaaggaa caauggucgg aggagugauu 60
gccgaaccca gcgcucagau gucaacugcg gcggacaugg ccuccggaaa gucgguggac 120
uccgaguggg aagccuucuu cucguuccac acguccguga acuggagcac cuccgaaacc 180
caaggaaaga uccucuucaa gcagucccug gguccccugc ugaacccgua ccuggagcac 240
aucagcaagc uguacgucgc uuggagcggg ucgaucgaag ugcgauuuuc caucucggga 300
agcggcgugu ucggugguaa acuggccgcc aucgucgugc cgccuggugu cgacccuguc 360
cagucaaccu ccaugcugca guacccgcac guccuguucg acgcaagaca aguggagcca 420
gugaucuucu ccaucccgga ccuccgcaac agccuguauc acuugauguc cgauaccgau 480
accacuuccc ucgugaucau gguguacaac gaucugauca acccguacgc caaugacucc 540
aacagcucgg guugcaucgu gaccgucgaa acgaagccug gcaucgauuu caaguuucau 600
cugcugaaac cgcccggauc caugcuuacu cacgggucca ucccuuccga ucugaucccc 660
aagagcuccu cccuguggau ugggaaccgc cacuggaccg auauuaccga uuucgugauu 720

```
cggccuuucg uguuccaagc caaccggcac uucgacuuca accaggagac ugccggcugg    780

ucaacuccac gguuccgccc auuggccgug acugugucgc agucaaaggg agccaagcuc    840

gggaacggca ucgccaccga cuacauugug ccuggaaucc ccgacggaug gccugauacu    900

accaucccca ccaagcugac cccuaccgga gauuacgcca ucaccuccuc cgacggcaau    960

gauauugaaa ccaagcugga auacgagaac gcggacguga uuaagaacaa caccaacuuc   1020

cgcuccaugu auaucugcgg aagccuccag agggcuuggg gcgacaagaa gaucagcaac   1080

accggguuca ucacuaccgg agugauuucu gacaacucca ucagcccuuc gaacacaauu   1140

gaccagucca agaucguggu guaccaggac aaccauguca auucggaggu ccagacuagc   1200

gacaucacuc uugccauccu gggcuacacc ggaauuggag aagaggccau aggcgccaac   1260

cgggacuccg ucgugagaau uuccgugcuu ccggaaacug gagcaagggg cggaaaucac   1320

cccaucuucu acaaaaauuc caugaagcug ggcuacguga ucuccuccau ugacguguuc   1380

aacucccaaa uccuccacac cucgcgccag cugucacuga acaacuacuu guugcccccu   1440

gacuccuucg cgguguaccg gauuauugac agcaacggau cauggucga cauugggauu    1500

gacagcgaug gguuuucauu cgugggcgug ucgucauuuc caaagcugga guuuccgcug   1560

uccgccucau acaugggcau ccagcucgca aagauccggc uggcguccaa cauccgguca   1620

uccaugacua agcuguga                                                 1638
```

<210> SEQ ID NO 13
<211> LENGTH: 1629
<212> TYPE: RNA
<213> ORGANISM: Artificial Sequence
<220> FEATURE:
<223> OTHER INFORMATION: codon optimized for feline

<400> SEQUENCE: 13

```
augacugccc cggaacaagg aacgaugguc ggaggaguga uugcagaacc gucagcacag     60

auguccaccg cugccgacau ggccacugga aagagcgugg acuccgaaug ggaagccuuc    120

uucuccuucc acacuucggu caacuggucg acuagcgaaa cccaggggaa gauuuuguuc    180

aagcaauccc ucggcccucu gcugaacccc uaccuggagc aucuggccaa gcuguacgug    240

gcauggucgg gcagcaucga agugcgcuuu agcauuuccg gcuccggagu guucgggggga   300

aagcuugcug ccauugucgu gccgccagga guggacccgg ugcaguccac uucuaugcuc    360

caauacccgc auguccuguu cgacgccaga cagguggagc cugugaucuu uugccugccg    420

gaucucaggu ccacccugua ucaccucaug uccgacaccg acaccaccuc gcucgugauc    480

augguguaca acgaccugau caaccccuac gcuaacgacg ccaacagcuc agguugcauu    540

gugacugucg aaaccaagcc aggcccugac uucaaguuuc auuugcugaa gccgcccggu    600

uccaugcuga cccacggcuc gaucccaucc gaccugaucc ccaagacgag cucccugugg    660

aucggaaacc gcuacugguc cgauauuacc gacuucguga ucagaccauu cguguuccaa    720

gccaaccgcc auuucgacuu caaccaggaa accgcaggau ggucgacccc ucgauuccgc    780

ccgauuucag ugaccaucac cgaacagaac ggcgcgaagc ugggaauugg cguggcgacc    840

gacuacaucg ugccgggaau cccggaugga uggccugaua cgaccauucc cggggagcug    900

aucccugccg gggacuacgc caucaccaac gguacuggaa acgacaucac cacugccacc    960

gguuacgaca ccgccgacau cauaaagaac aacaccaacu ucagaggaau guacauuugc   1020

ggcucccugc aacgcgcuug ggugacaaa aagaucucga acacugccuu caucacaaca    1080
```

-continued gcgacucugg acggcgauaa caacaacaag aucaauccuu guaauaccau cgaccagucc 1140
aaaaucgugg uguuccagga uaaccacgug ggaaagaagg cgcagaccuc cgacgacacu 1200
cuggcgcugc uuggcuacac cgggaucggc gagcaggcca uuggaagcga ucgggaucgg 1260
gucgugcgga ucuccacccu ccccgagacu ggagcaaggg gaggcaacca ccccaucuuu 1320
uacaaaaaca gcauuaagcu cggauacguc auccgcucca ucgauguguu caacucucaa 1380
auccugcaca cuucgcggca gcugucccug aaccacuacc ucuugccgcc cgacuccuuc 1440
gccgucuacc ggaucauuga uucgaacggg agcugguucg acaucggcau ugauagcgau 1500
ggcuucucgu uugugggcgu gucgggcuuc gggaagcugg aguucccacu gagcgccuca 1560
uacaugggua uccagcuggc caagaucagg cuggccucca acauccgcuc accuaugacu 1620
aagcuguga 1629

<210> SEQ ID NO 14
<211> LENGTH: 1929
<212> TYPE: RNA
<213> ORGANISM: Artificial Sequence
<220> FEATURE:
<223> OTHER INFORMATION: codon optimized for feline

<400> SEQUENCE: 14
auggagucac caacacaccc uaaaccuucu aaagacaaaa cccucucgug gaaucucgcc 60
uuccuugugg gcauccuguu cacaaucgac aucggcaugg ccaacccuuc gccgcaucag 120
aucuacaaug ugacaugggu cauuacuaau gugcagacaa acacccaggc aaaugcuacu 180
ucuaugcuug guacucugac ugaugcuuau ccaacccugc acgucgaccu uugcgaucuc 240
gucggugaca caugggagcc caucgugcug aauccaacua augucaaaca uggugccagg 300
uauucuucua gcaaauacgg guguaagacc acugaucgga agaaacagca acaaaccuac 360
ccauucuacg ugugcccggg ucacgcaccg ucccugggcuc cgaagggaac acauugaggg 420
ggagcccaag acgguuuuug cgcugcuugg gguugugaaa caaccggaga agccuggugg 480
aagccuaccu caucuuggga cuacauuacu gugaaaagag gcucuagcca ggauaacagc 540
ugcgaaggaa aguguaaucc ccuggugcuu caauucaccc agaaaggccg gcaggcauca 600
ugggauggac cgaaaaugug gggacuuaga cucuaucgca ccggauacga ccccaucgcu 660
cuguuuacug ugucacgcca agucuccacc auuacuccgc cacaggccau ggggccgaau 720
cugguccucc ccgaucagaa gccacccuca cggcaaaguc aaaccggcuc aaaaguggcc 780
acccaacggc cccagacaaa ugaguccgca ccuaggucag uggcaccuac aacaaugggu 840
ccaaagcgga ucggaaccgg agacaggcuc auuaaccucg ugcaagggac uuaucuggcc 900
cuuaacgcua cugaccccaa caagaccaag gauugcuggc ucugccuugu gagcagaccu 960
ccuuacuaug aggggaucgc cauucucgga aacuacucaa aucagaccaa ccccccuccg 1020
ucgugucuga gcacccccca gcacaagcuu acuauuucag aagucagugg acagggaaug 1080
ugcaucggaa ccgugccaaa gacucaucaa gcccuuugca acaaaacuca acaagggcac 1140
acuggagcuc auuaucucgc cgcaccuaac gggaccuacu gggcuugcaa uacuggauug 1200
accccgugua ucucuauggc cgugcugaau uggacuuccg acuucugcgu gcuuauugag 1260
cuuuggccua gagugacaua ccaucagccu gaguacgucu auacccauuu cgccaaggca 1320
gucagauucc ggcgggagcc uaucucccug acuguggccu ugaugcucgg uggacugaca 1380
gugggaggaa uugcagcugg agucggaacu ggaaccaagg cccugcucga aacugcucag 1440
uuccggcagc ugcagauggc caugcacacu gacauccagg cucuggagga aucaauuuca 1500

-continued

```
gcccuugaga aaagcuugac cucgcugucu gaaguggucc uccaaaacag gcgcgguuug   1560

gacauccugu uccuucaaga ggguggucug ugcgccgcuc ucaaggagga augcuguuuc   1620

uacgcugacc auaccgggcu ggugcgcgau aacauggcaa agcugcggga acgcuugaaa   1680

cagaggcagc aacuguucga cucucagcag ggaugguucg agggcugguu uaacaagagc   1740

ccaugguuua ccacucugau cucuucaauc augggguccac ugcucauccu gcuucugauu  1800

cuucucuucg gaccguguau ucucaacagg cugguugcagu uugucaagga cagaaucucg  1860

gugguccagg cccugauucu uacucagcag uaucagcaga uuaagcagua cgaccccgau   1920

cggccuuga                                                            1929
```

```
<210> SEQ ID NO 15
<211> LENGTH: 1233
<212> TYPE: RNA
<213> ORGANISM: Artificial Sequence
<220> FEATURE:
<223> OTHER INFORMATION: codon optimized for feline

<400> SEQUENCE: 15

aauccuaguc cacaccaaau auauaaugua acuuggguaa uaaccaaugu acaaacuaac     60

acccaagcua acgccaccuc uauguuagga accuuaaccg augccuaccc uacccuacau    120

guugacuuau gugaccuagu gggagacacc ugggaaccua uaguccuaaa cccaaccaau    180

guaaaacacg gggcacguua cuccuccuca aaauauggau guaaaacuac agauagaaaa    240

aaacagcaac agacauaccc cuuuuacguc ugccccggac augcccccuc guuggggcca    300

aagggaacac auuguggagg ggcacaagau ggguuuugug ccgcaugggg augugagacc    360

accggagaag cuuggugugaa gcccaccucc ucaugggacu auaucacagu aaaaagaggg   420

aguagucagg acaauagcug ugagggaaaa ugcaaccccc ugguuuugca guucacccag    480

aagggaagac aagccucuug ggacggaccu aagauguggg gauugcgacu auaccguaca    540

ggauaugacc cuaucgcuuu auucacggug ucccggcagg uaucaaccau uacgccgccu    600

caggcaaugg gaccaaaccu agucuuaccu gaucaaaaac ccccaucccg acaaucucaa    660

acagggucca aaguggcgac ccagaggccc caaacgaaug aaagcgcccc aaggucuguu    720

gcccccacca ccaugggucc caaacggauu gggaccggag auagguuaau aaauuuagua    780

caagggacau accuagccuu aaaugccacc gaccccaaca aaacuaaaga cuguuggcuc    840

ugccugguuu cucgaccacc cuauuacgaa gggauugcaa ucuuagguaa cuacagcaac    900

caaacaaacc cccccccauc cugccuaucu acuccgcaac acaaacuaac uauaucugaa    960

guaucagggc aaggaaugug cauagggacu guuccuaaaa cccaccaggc uuugugcaau   1020

aagacacaac agggacauac aggggcgcac uaucuagccg cccccaacgg caccuauugg   1080

gccuguaaca cuggacucac cccaugcauu uccauggcgg ugcucaauug gaccucugau   1140

uuuuguguicu uaaucgaauu auggcccaga gugacuuacc aucaacccga auauguguac  1200

acacauuuug ccaaagcugu cagguuccga aga                                 1233
```

```
<210> SEQ ID NO 16
<211> LENGTH: 1575
<212> TYPE: RNA
<213> ORGANISM: Artificial Sequence
<220> FEATURE:
<223> OTHER INFORMATION: codon optimized for human
```

-continued

<400> SEQUENCE: 16

```
auggugccgc aggcucuccu guuuguccccc cuucuggucu uuccauugug uuuugggaaa     60
uucccuaucu acacaauucc ggacaaguug ggacccugga gcccaauuga cauucaucau    120
cucagcugcc cgaacaauuu ggucguggag gacgaaggau gcaccaaccu gucgggguuc    180
uccuacaugg aauugaaagu cggauacauc agugccauua agaugaacgg guucacuugc    240
acaggcgucg ugacugaagc ugagacauac acuaacuucg ugggauaugu cacuaccacu    300
uucaaaagaa agcauuuccg cccuacuccu gaugcuugua gggccgcaua caacuggaag    360
auggccggug accccagaua ugaggaauca cuucacaauc cguacccuga cuaccacugg    420
cuucggacug ucaaaaccac caaggaguca cucgugauca uuaguccaag uguggcugau    480
cuugacccau acgaccgguc acuucacuca cggguguucc cgggggggaa uugcucuggu    540
gucgcagugu cgucaaccua cugcuccaca aaccacgauu acaccauuug gaugccagaa    600
aauccucggc uugguauguc augugacauu uucaccaauu cucgggggaa gagggcuucc    660
aaagggucug aaacuugcgg cuuugucgau gagcggggcu uguauaaguc acuuaaaggu    720
gcuugcaaac ucaagcuuug uggugucuug ggauugagau ugauggaugg aacuuggguc    780
gcaaugcaga cuucuaacga aaccaaaugg ugcccucccg gacagcuugu gaauuugcau    840
gacuuucgcu cugacgaaau ugagcaucuu gucgucgagg aguuggucaa gaagcgggaa    900
gagugucugg augcuuugga aucaaucaug accaccaagu cagugucuuu cagacggcuc    960
ucacaucuua ggaaauuggu gccagguuuu ggaaaagcau auaccauuuu caacaagacc   1020
cuuauggaag ccgaugcuca cuacaagucu gucaggacuu ggaaugagau caucccgucu   1080
aaagggugucc uuagggucgg agggagaugu cauccucaug ucaacggagu cuuuuucaau   1140
gguaucauuc uuggaccuga cggaaauguc cuuaucccug agaugcaauc uucccuccuc   1200
cagcaacaca uggaacuucu ugucucaucg gucauccccc uuaugcaccc ccuggcugac   1260
ccaucaaccg uguucaagaa cggugacgag gcagaggauu uugucgaggu ccaccuuccc   1320
gaugugcaug aacggaucuc uggugucgac cuuggacucc cuaacugggg aaaguauguc   1380
cuucugucgg caggagcccu gacugccuug auguugauua ucuuccugau gacuuguugg   1440
aggagaguca aucggucgga gccaacacaa cauaaucuca gaggaacagg aagggaggug   1500
ucagucacac cccaaagcgg gaagaucauu ucgucuuggg agucauacaa gagcggaggu   1560
gaaaccggac uguga                                                    1575
```

FELINE CALICIVIRUS VACCINE

CROSS-REFERENCE TO RELATED APPLICATIONS

This application is a national stage entry under 35 U.S.C. § 371 of PCT/EP2018/080096, filed on Nov. 5, 2018, which claims priority under 35 U.S.C. § 119(e) of provisional application U.S. Ser. No. 62/596,508 filed Dec. 8, 2017, U.S. Ser. No. 62/582,050, filed Nov. 6, 2017, U.S. Ser. No. 62/581,955 filed Nov. 6, 2017, and U.S. Ser. No. 62/599,401 filed Dec. 15, 2017, the contents of which are hereby incorporated by reference in their entireties.

FIELD OF THE INVENTION

The present invention relates to new vaccines for feline calicivirus. Methods of making and using the vaccines alone or in combination with other protective agents are also provided.

BACKGROUND

Feline calicivirus (FCV) is usually associated with upper respiratory disease in cats. FCV together with feline herpesvirus are thought to be responsible for approximately 80% of all feline respiratory disease. The most common characteristic and clinical signs of FCV infection is the development of vesicles (ulcers) on the tongue and oral mucosa. These vesicles begin as small, individual ulcers which may spread and affect a large part of the tongue. The vesicles usually do not interfere with eating and drinking, and normally heal without incident. Fever often also is observed in infected cats.

Certain strains of FCV also cause a disease in cats known as limping syndrome. Limping syndrome is characterized by fever, joint and muscle soreness (limping), and occasional lingual/oral ulceration. In addition, some strains of FCV have been associated with chronic stomatitis in infected cats. Other, less common clinical signs are conjunctivitis, rhinitis, and occasionally pneumonia. Cats infected with FCV may become persistently infected, and may shed infectious virus for long periods of time.

FCV comprises a single-stranded, positive-sense RNA genome consisting of three open reading frames (ORFs). The genome is polyadenylated at the 3' end and bound by a virally-encoded protein at the 5'-end. The first open reading frame encodes a viral protease and an RNA-dependent RNA polymerase, which are expressed on a single polypeptide. This polypeptide then is post-translationally cleaved by the viral protease. The second open reading frame encodes the major capsid protein (i.e., the FCV capsid protein), which has six regions denoted as A-F [Scott et al., 60 *Am. J. Vet. Res.*: 652-658 (1999)]. Region A is cleaved to produce the mature capsid protein. Whereas regions B, D, and F of ORF2 are relatively conserved between FCV isolates, regions C and E are variable, with region E of ORF2 containing the major B-cell epitopes [see, Radford et al., 38(2) *Vet Res.*: 319-335 (2007)]. ORF 3 encodes a minor structural protein [Sosnovtsev and Green, 277 *Virology*: 193-203 (2000)].

A number of vector strategies have been employed through the years for vaccines in an effort to protect against certain pathogens. One such vector strategy includes the use of alphavirus-derived replicon RNA particles (RP) [Vander Veen, et al. *Anim Health Res Rev.* 13(1):1-9. (2012) doi: 10.1017/S1466252312000011; Kamrud et al., *J Gen Virol.* 91(Pt 7):1723-1727 (2010)] which have been developed from several different alphaviruses, including Venezuelan equine encephalitis virus (VEE) [Pushko et al., *Virology* 239:389-401 (1997)], Sindbis (SIN) [Bredenbeek et al., *Journal of Virology* 67:6439-6446 (1993)], and Semliki Forest virus (SFV) [Liljestrom and Garoff, Biotechnology (NY) 9:1356-1361 (1991)]. RP vaccines deliver propagation-defective alphavirus RNA replicons into host cells and result in the expression of the desired antigenic transgene(s) in vivo [Pushko et al., *Virology* 239(2):389-401 (1997)]. RPs have an attractive safety and efficacy profile when compared to some traditional vaccine formulations [Vander Veen, et al. *Anim Health Res Rev.* 13(1):1-9. (2012)]. The RP platform has been used to encode pathogenic antigens and is the basis for several USDA-licensed vaccines for swine and poultry.

Although, long characterized as belonging to a single serotype, FCV isolates are antigenically highly variable, and antibodies from cats vaccinated with older vaccine strains of FCV, such as FCV F9, do not efficiently neutralize all current field isolates. Moreover, new FCV strains associated with systemic disease and high mortality have been identified [see e.g., U.S. Pat. No. 7,449,323 B2]. These "virulent systemic" (VS-FCV) isolates are responsible for localized outbreaks, and current vaccines also do not appear to protect cats from disease caused by these strains. This has led to concern that cats vaccinated with current vaccine strains are not fully protected from disease caused by such "antigenically heterologous" FCV strains, and that these heterologous strains may be responsible for outbreaks of disease, even in vaccinated cats. It is therefore desirable to develop new vaccines that stimulate more broadly reactive virus-neutralizing (VN) antibodies, and therefore provide better protection against new field isolates.

The citation of any reference herein should not be construed as an admission that such reference is available as "prior art" to the instant application.

SUMMARY OF THE INVENTION

Accordingly, the present invention provides vectors that encode one or more feline calicivirus (FCV) antigens. Such vectors can be used in immunogenic compositions comprising these vectors. The immunogenic compositions of the present invention may be used in vaccines. In one aspect of the present invention, a vaccine protects the vaccinated subject (e.g., mammal) against FCV. In a particular embodiment of this type, the vaccinated subject is a feline. In a more particular embodiment, the vaccinated subject is a domestic cat. The present invention further provides combination vaccines for eliciting protective immunity against FCV and other diseases, e.g., other infectious diseases in cats. Methods of making and using the immunogenic compositions and vaccines of the present invention are also provided.

In specific embodiments, the vector is an alphavirus RNA replicon particle that encodes one or more antigens that originate from a feline pathogen. In particular embodiments, the feline pathogen is a feline calicivirus (FCV). In specific embodiments of this type, the alphavirus RNA replicon particle encodes an FCV capsid protein. In related embodiments, the alphavirus RNA replicon particle encodes an antigenic fragment of an FCV capsid protein. In certain embodiments, the FCV capsid protein is an FCV F9-Like capsid protein. In other embodiments, the alphavirus RNA replicon particle encodes an antigenic fragment of an FCV F9-Like capsid protein. In yet other embodiments, the FCV capsid protein is a virulent systemic FCV (VS-FCV) capsid protein. In still other embodiments, the alphavirus RNA replicon particle encodes an antigenic fragment of a VS- FCV capsid protein. In yet other embodiments, the alphavirus RNA replicon particle encodes both the FCV F9-Like capsid protein or antigenic fragment thereof and the VS-FCV capsid protein or an antigenic fragment thereof.

In still more particular embodiments, the alphavirus RNA replicon particle is a Venezuelan Equine Encephalitis (VEE) alphavirus RNA replicon particle. In yet more specific embodiments the VEE alphavirus RNA replicon particle is a TC-83 VEE alphavirus RNA replicon particle. In other embodiments, the alphavirus RNA replicon particle is a Sindbis (SIN) alphavirus RNA replicon particle. In still other embodiments, the alphavirus RNA replicon particle is a Semliki Forest virus (SFV) alphavirus RNA replicon particle. In an alternative embodiment a naked DNA vector comprises a nucleic acid construct that encodes one or more antigens that originate from a feline pathogen. In particular embodiments of this type, the naked DNA vectors comprise a nucleic acid construct that encodes an FCV capsid protein, or antigenic fragment thereof.

In certain embodiments, an alphavirus RNA replicon particle of the present invention encodes one or more FCV antigens or antigenic fragments thereof. In particular embodiments of this type, the alphavirus RNA replicon particles encode two to four FCV antigens or antigenic fragments thereof. In related embodiments an alphavirus RNA replicon particle of the present invention encodes one or more FCV antigens or antigenic fragments thereof and one or more non-FCV antigens or antigenic fragments thereof. In specific embodiments of this type, the alphavirus RNA replicon particles encode one or more FCV capsid proteins or antigenic fragments thereof and one to three non-FCV antigens or antigenic fragments thereof. In more specific embodiments, the alphavirus RNA replicon particles encode the VS-FCV capsid protein or an antigenic fragment thereof and the FCV-F9-like capsid protein or an antigenic fragment thereof and one to three non-FCV antigens or antigenic fragments thereof.

In another aspect, the present invention provides immunogenic compositions that comprise alphavirus RNA replicon particles that encode one or more FCV antigens or antigenic fragments thereof. In related embodiments, the immunogenic compositions comprise alphavirus RNA replicon particles that encode two to four FCV antigens or antigenic fragments thereof. In particular embodiments of this type, the alphavirus RNA replicon particle encodes an FCV capsid protein. In other embodiments, the alphavirus RNA replicon particle encodes an antigenic fragment of an FCV capsid protein. In certain embodiments, the immunogenic compositions comprise an alphavirus RNA replicon particle that encodes an FCV F9-Like capsid protein. In other embodiments, the immunogenic compositions comprise an alphavirus RNA replicon particle that encodes an antigenic fragment of an FCV F9-Like capsid protein. In yet other embodiments, the immunogenic compositions comprise an alphavirus RNA replicon particle that encodes a virulent systemic FCV (VS-FCV) capsid protein. In still other embodiments, the immunogenic compositions comprise an alphavirus RNA replicon particle that encodes an antigenic fragment of a VS-FCV capsid protein. In yet other embodiments, the immunogenic compositions comprise an alphavirus RNA replicon particle that encodes both the FCV F9-Like capsid protein or antigenic fragment thereof and the VS-FCV capsid protein or an antigenic fragment thereof. In more particular embodiments, the immunogenic composition comprises alphavirus RNA replicon particles that are Venezuelan Equine Encephalitis (VEE) alphavirus RNA replicon particles. In yet more specific embodiments the immunogenic compositions comprise VEE alphavirus RNA replicon particles that are TC-83 VEE alphavirus RNA replicon particles.

In still other embodiments, the immunogenic composition comprises two or more sets of alphavirus RNA replicon particles. In certain embodiments of this type, one set of alphavirus RNA replicon particles encodes a first antigen, whereas the other set of alphavirus RNA replicon particles encodes a second antigen. In particular embodiments of this type, the first set of alphavirus RNA replicon particles encodes one or more FCV antigens or antigenic fragments thereof, and the second set of alphavirus RNA replicon particles encode one or more FeLV antigens or antigenic fragments thereof. In certain embodiments, the FCV antigen originates from a virulent systemic feline calicivirus (VS-FCV) isolate. In other embodiments the FCV antigen originates from a classical (F9-like) feline calicivirus isolate. In yet other embodiments, the second set of alphavirus RNA replicon particles encode two FCV antigens or antigens thereof, one of which originates from a virulent systemic FCV isolate, whereas the other originates from a F9-like FCV. In still other embodiments, an immunogenic composition comprises a first set of alphavirus RNA replicon particles that encode an FCV F9-Like capsid protein or antigenic fragment thereof and the second set of alphavirus RNA replicon particles encode a VS-FCV capsid protein or an antigenic fragment thereof. In related embodiments, an immunogenic composition comprises a first set of alphavirus RNA replicon particles that encode a VS-FCV capsid protein or antigenic fragment thereof and the second set of alphavirus RNA replicon particles encode a FeLV glycoprotein (e.g., gp85) or an antigenic fragment thereof, (e.g., FeLV glycoprotein gp70 and/or gp45).

In yet other embodiments, the immunogenic composition comprises one set of alphavirus RNA replicon particles that encode a first antigen, another set of alphavirus RNA replicon particles that encode a second antigen, and a third set of alphavirus RNA replicon particles that encode a third antigen. In a particular embodiment of this type, the first set of alphavirus RNA replicon particles encode an FCV antigen (e.g., the capsid protein) which originates from a classical (F9-like) feline calicivirus or an antigenic fragment thereof, the second set of alphavirus RNA replicon particles encode an FCV antigen (e.g., the capsid protein), which originates from a virulent systemic feline calicivirus or an antigenic fragment thereof, and the third set of alphavirus RNA replicon particles encode a FeLV antigen (e.g., the FeLV gp85) or an antigenic fragment thereof.

Accordingly, in particular embodiments in which the immunogenic compositions comprise multiple sets (e.g., 2-10) of alphavirus RNA replicon particles, in which the first set of alphavirus RNA replicon particles encodes an FCV F9-Like capsid protein or antigenic fragment thereof and/or a VS-FCV capsid protein or an antigenic fragment thereof, and the one or more other sets of alphavirus RNA replicon particles encode one or more non-FCV antigens.

In certain embodiments of this type, the non-FCV antigen or antigenic fragment thereof is a protein antigen that originates from feline herpesvirus (FHV). In other embodiments, the non-FCV antigen is a protein antigen that originates from feline leukemia virus (FeLV). In yet other embodiments, the non-FCV antigen is a protein antigen that originates from feline pneumovirus (FPN). In still other embodiments, the non-FCV antigen is a protein antigen that originates from feline parvovirus (FPV). In yet other embodiments, the non-FCV antigen is a protein antigen that originates from rabies virus. In still other embodiments, the non-FCV antigen is a protein antigen that originates from feline infectious peritonitis virus (FIPV). In yet other embodiments, the non-FCV antigen is a protein antigen that originates from feline immunodeficiency virus. In still other embodiments, the non-FCV antigen is a protein antigen that originates from borna disease virus (BDV). In yet other embodiments, the non-FCV antigen is a protein antigen that originates from feline influenza virus. In still other embodiments, the non-FCV antigen is a protein antigen that originates from feline panleukopenia virus (FPLV). In yet other embodiments the non-FCV antigen is a protein antigen that originates from feline coronavirus (FCoV). In still other embodiments the non-FCV antigen is a protein antigen that originates from feline rhinotracheitis virus (FVR). In yet other embodiments the non-FCV antigen is a protein antigen that originates from *Chlamydophila felis.*

The present invention also includes all of the alphavirus RNA replicon particles of the present invention, the naked DNA vectors, the nucleic acid constructs of the present invention including synthetic messenger RNA, and RNA replicons, as well as all of the immunogenic compositions and/or vaccines that comprise the nucleic acid constructs (e.g., synthetic messenger RNA, RNA replicons), the alphavirus RNA replicon particles, and/or the naked DNA vectors of the present invention.

In particular embodiments, a nucleic acid construct of the present invention encodes one or more FCV antigens or antigenic fragments thereof. In related embodiments of this type, the nucleic acid construct encodes two to four FCV antigens or antigenic fragments thereof. In other embodiments, alphavirus RNA replicon particles comprise a nucleic acid construct that encodes one or more FCV antigens or antigenic fragments thereof. In particular embodiments, alphavirus RNA replicon particles comprise a nucleic acid construct that encodes two to four FCV antigens or antigenic fragments thereof.

In still other embodiments, the immunogenic compositions comprise alphavirus RNA replicon particles and/or naked DNA vectors that comprise a nucleic acid construct that encodes two to four FCV antigens or antigenic fragments thereof. In particular embodiments of this type, the alphavirus RNA replicon particles encode an FCV F9-Like capsid protein or antigenic fragment thereof and/or a VS-FCV capsid protein or an antigenic fragment thereof and an FeLV glycoprotein (gp85) or an antigenic fragment thereof. In particular embodiments of this type, the antigenic fragment of gp85 is the FeLV glycoprotein gp70. In other related embodiments, the antigenic fragment of gp85 is the FeLV glycoprotein gp45. In more particular embodiments, the immunogenic composition comprises alphavirus RNA replicon particles that are Venezuelan Equine Encephalitis (VEE) alphavirus RNA replicon particles. In yet more specific embodiments the VEE alphavirus RNA replicon particles are TC-83 VEE alphavirus RNA replicon particles.

In yet other embodiments, the immunogenic composition comprises two or more sets of alphavirus RNA replicon particles and/or naked DNA vectors. In particular embodiments of this type, one set of alphavirus RNA replicon particles and/or naked DNA vectors comprise a first nucleic acid construct, whereas the other set of alphavirus RNA replicon particles and/or naked DNA vectors comprise a second nucleic acid construct. In a specific embodiment of this type the first nucleic acid construct encodes an FCV antigen or an antigenic fragment thereof, and the second nucleic acid construct encodes a feline calicivirus (FCV) antigen or an antigenic fragment thereof. In certain embodiments of this type, the FCV antigen originates from a virulent systemic feline calicivirus (VS-FCV) isolate. In other embodiments the FCV antigen originates from a classical (F9-like) feline calicivirus isolate. In yet other embodiments, the second nucleic acid construct encodes two FCV antigens, one of which originates from a virulent systemic feline calicivirus isolate, whereas the other originates from a classical (F9-like) feline calicivirus isolate.

In still other embodiments, the immunogenic composition comprises one set of alphavirus RNA replicon particles and/or naked DNA vectors that comprise a first nucleic acid construct, another set of alphavirus RNA replicon particles and/or naked DNA vectors that comprise a second nucleic acid construct, and a third set of alphavirus RNA replicon particles and/or naked DNA vectors that comprise a third nucleic acid construct. In a particular embodiment of this type, the first nucleic acid construct encodes a FeLV antigen or an antigenic fragment thereof, the second nucleic acid construct encodes a feline calicivirus (FCV) antigen which originates from a virulent systemic feline calicivirus or an antigenic fragment thereof, and the third nucleic acid construct encodes a feline calicivirus (FCV) antigen which originates from a classical (F9-like) feline calicivirus or an antigenic fragment thereof.

In yet other embodiments, the immunogenic composition comprises one set of alphavirus RNA replicon particles and/or naked DNA vectors that comprise a first nucleic acid construct, another set of alphavirus RNA replicon particles and/or naked DNA vectors that comprise a second nucleic acid construct, a third set of alphavirus RNA replicon particles and/or naked DNA vectors that comprise a third nucleic acid construct, and a fourth set of alphavirus RNA replicon particles and/or naked DNA vectors that comprise a fourth nucleic acid construct. In particular embodiments of this type, the first nucleic acid construct encodes both a feline calicivirus (FCV) antigen which originates from a virulent systemic feline calicivirus or an antigenic fragment thereof, and a feline calicivirus (FCV) antigen which originates from a classical (F9-like) feline calicivirus or an antigenic fragment thereof.

In still other embodiments, the immunogenic composition comprises a set of alphavirus RNA replicon particles and/or naked DNA vectors that comprise a first nucleic acid construct, another set of alphavirus RNA replicon particles and/or naked DNA vectors that comprise a second nucleic acid construct, a third set of alphavirus RNA replicon particles and/or naked DNA vectors that comprise a third nucleic acid construct, a fourth set of alphavirus RNA replicon particles and/or naked DNA vectors that comprise a fourth nucleic acid construct, and a fifth set of alphavirus RNA replicon particles and/or naked DNA vectors that comprise a fifth nucleic acid construct. In such embodiments, the nucleotide sequences of the first nucleic acid construct, the second nucleic acid construct, third nucleic acid construct, the fourth nucleic acid construct, and the fifth nucleic acid construct are all different. In particular embodiments of this type, the first nucleic acid construct encodes both a feline calicivirus (FCV) antigen which originates from a virulent systemic feline calicivirus or an antigenic fragment thereof, and a feline calicivirus (FCV) antigen which originates from a classical (F9-like) feline calicivirus or an antigenic fragment thereof.

Accordingly, an immunogenic composition of the present invention can contain alphavirus RNA replicon particles and/or naked DNA vectors that comprise a nucleic acid construct that encodes at least one non-FCV antigen for eliciting protective immunity to a non-FCV pathogen. In particular embodiments of this type, the non-FCV antigen is a protein antigen that originates from feline herpesvirus (FHV). In other embodiments, the non-FCV antigen is a protein antigen that originates from feline leukemia virus (FeLV). In yet other embodiments, the non-FCV antigen is a protein antigen that originates from feline pneumovirus (FPN). In still other embodiments, the non-FCV antigen is a protein antigen that originates from feline parvovirus (FPV). In yet other embodiments, the non-FCV antigen is a protein antigen that originates from feline infectious peritonitis virus (FIPV). In still other embodiments, the non-FCV antigen is a protein antigen that originates from feline immunodeficiency virus. In yet other embodiments, the non-FCV antigen is a protein antigen that originates from rabies virus. In still other embodiments, the non-FCV antigen is a protein antigen that originates from borna disease virus (BDV). In yet other embodiments, the non-FCV antigen is a protein antigen that originates from feline influenza virus. In still other embodiments, the non-FCV antigen is a protein antigen that originates from feline panleukopenia virus (FPLV). In yet other embodiments the non-FCV antigen is a protein antigen that originates from feline coronavirus (FCoV). In still other embodiments the non-FCV antigen is a protein antigen that originates from feline rhinotracheitis virus (FVR). In still other embodiments the non-FCV antigen is a protein antigen that originates from *Chlamydophila felis*.

The present invention further provides combination immunogenic compositions and/or vaccines (multivalent vaccines) that include alphavirus RNA replicon particles that encode one or more antigens or antigenic fragments thereof originating from FCV together (e.g., the FCV capsid protein) and further comprise one or more modified live/attenuated or killed feline pathogens. In particular embodiments, the immunogenic compositions further comprise a modified live or killed *Chlamydophila felis* combined with alphavirus RNA replicon particles that encode an antigen or antigenic fragment thereof originating from FeLV. In other embodiments, the immunogenic compositions further comprise a modified live or killed feline rhinotracheitis Virus (FVR) combined with alphavirus RNA replicon particles that encode an antigen or antigenic fragment thereof originating from FeLV. In yet other embodiments, the immunogenic compositions further comprise a modified live or killed feline panleukopenia virus (FPL) combined with alphavirus RNA replicon particles that encode an antigen or antigenic fragment thereof originating from FeLV. In certain embodiments, a vaccine comprises an immunologically effective amount of one or more of these immunogenic compositions.

In more specific embodiments, the immunogenic compositions comprise alphavirus RNA replicon particles that encode a capsid protein or antigenic fragment thereof originating from VS-FCV and further comprise a modified live or killed F9-like FCV. In still other embodiments, the immunogenic compositions comprise alphavirus RNA replicon particles that encode a capsid protein or antigenic fragment thereof originating from VS-FCV and further comprise a modified live or killed F9-like FCV, a modified live or killed *Chlamydophila felis*, a modified live or killed FVR, and a modified live or killed FPL. In related embodiments, the immunogenic composition also comprises alphavirus RNA replicon particles that encode an antigen or antigenic fragment thereof originating from FeLV. In particular embodiments of this type, the feline antigen of the FeLV is the FeLV viral glycoprotein (gp85). In certain embodiments, the present invention provides vaccines that comprise an immunologically effective amount of one or more of these immunogenic compositions.

In particular embodiments, an alphavirus RNA replicon particle of the present invention encodes a VS-FCV capsid protein or antigenic fragment thereof. In specific embodiments of this type, the VS-FCV capsid protein comprises an amino acid sequence comprising 95% identity or more with the amino acid sequence of SEQ ID NO: 2. In more specific embodiments of this type, the VS-FCV capsid protein comprises an amino acid sequence comprising 98% identity or more with the amino acid sequence of SEQ ID NO: 2. In even more specific embodiments of this type, the VS-FCV capsid protein comprises the amino acid sequence of SEQ ID NO: 2. In specific embodiments of this type the VS-FCV capsid protein is encoded by the nucleotide sequence of SEQ ID NO: 1 or SEQ ID NO: 12.

In related embodiments, an alphavirus RNA replicon particle of the present invention encodes a FCV F9-Like capsid protein or antigenic fragment thereof. In specific embodiments of this type, the FCV F9-Like capsid protein comprises an amino acid sequence comprising 95% identity or more with the amino acid sequence of SEQ ID NO: 4. In more specific embodiments of this type, the FCV F9-Like capsid protein comprises an amino acid sequence comprising 98% identity or more with the amino acid sequence of SEQ ID NO: 4. In even more specific embodiments of this type, the FCV F9-Like capsid protein comprises the amino acid sequence of SEQ ID NO: 4. In specific embodiments of this type the FCV F9-Like capsid protein is encoded by the nucleotide sequence of SEQ ID NO: 3 or SEQ ID NO: 13.

In certain embodiments an alphavirus RNA replicon particle of the present invention encodes a FeLV glycoprotein (gp85). In specific embodiments of this type, the FeLV glycoprotein gp85 comprises an amino acid sequence comprising 95% identity or more with the amino acid sequence of SEQ ID NO: 6. In more specific embodiments of this type, the FeLV glycoprotein (gp85) comprises the amino acid sequence of SEQ ID NO: 6. In even more specific embodiments of this type the FeLV glycoprotein (gp85) is encoded by the nucleotide sequence of SEQ ID NO: 5 or SEQ ID NO: 14.

In related embodiments, the FeLV glycoprotein gp70 comprises an amino acid sequence comprising 95% identity or more with the amino acid sequence of SEQ ID NO: 8. In more specific embodiments of this type, the FeLV glycoprotein (gp85) comprises the amino acid sequence of SEQ ID NO: 8. In even more specific embodiments of this type the FeLV glycoprotein (gp70) is encoded by the nucleotide sequence of SEQ ID NO: 7 or SEQ ID NO: 15.

In yet other embodiments an alphavirus RNA replicon particle of the present invention encodes a rabies virus glycoprotein (G). In specific embodiments of this type, the rabies virus glycoprotein comprises an amino acid sequence comprising 95% identity or more with the amino acid sequence of SEQ ID NO: 10. In more specific embodiments of this type, the rabies virus glycoprotein (G) comprises the amino acid sequence of SEQ ID NO: 10. In even more specific embodiments of this type the rabies virus glycoprotein (G) is encoded by the nucleotide sequence of SEQ ID NO: 9 or SEQ ID NO: 16.

The present invention further comprises vaccines, including multivalent vaccines, comprising the immunogenic compositions of the present invention. In particular embodiments, the vaccines are nonadjuvanted vaccine. In certain embodiments, the vaccine aids in the prevention of disease due to FCV. In related embodiments, antibodies are induced in a feline subject when the feline is immunized with the vaccine.

The present invention also provides methods of immunizing a feline against a feline pathogen, e.g., FCV, comprising administering to the feline an immunologically effective amount of a vaccine or multivalent of the present invention. In particular embodiments the vaccine is administered via intramuscular injection. In alternative embodiments the vaccine is administered via subcutaneous injection. In other embodiments the vaccine is administered via intravenous injection. In still other embodiments the vaccine is administered via intradermal injection. In yet other embodiments the vaccine is administered via oral administration. In still other embodiments the vaccine is administered via intranasal administration. In specific embodiments, the feline is a domestic cat.

The vaccines and multivalent vaccines of the present invention can be administered as a primer vaccine and/or as a booster vaccine. In specific embodiments, a vaccine of the present invention is administered as a one shot vaccine (one dose), without requiring subsequent administrations. In certain embodiments, in the case of the administration of both a primer vaccine and a booster vaccine, the primer vaccine and the booster vaccine can be administered by the identical route. In certain embodiments of this type, the primer vaccine and the booster vaccine are both administered by subcutaneous injection. In alternative embodiments, in the case of the administration of both a primer vaccine and a booster vaccine, the administration of the primer vaccine can be performed by one route and the booster vaccine by another route. In certain embodiments of this type, the primer vaccine can be administered by subcutaneous injection and the booster vaccine can be administered orally.

The invention further provides for a method of immunizing a feline against FCV comprising injecting the feline with an immunologically effective amount of the above described vaccines. In particular embodiments the vaccines can include from about $1\times10^4$ to about $1\times10^{10}$ RPs or higher, for example. In more particular embodiments the vaccines can include from about $1\times10^5$ to about $1\times10^9$ RPs. In even more particular embodiments the vaccines can include from about $1\times10^6$ to about $1\times10^8$ RPs. In particular embodiments the feline is a domestic cat.

In particular embodiments the vaccines of the present invention are administered in 0.05 mL to 3 mL doses. In more particular embodiments the dose administered is 0.1 mL to 2 mLs. In still more particular embodiments the dose administered is 0.2 mL to 1.5 mLs. In yet other embodiments the dose administered is 0.5 mL to 2.0 mLs. In still other embodiments the dose administered is 0.3 to 1.0 mLs. In yet more particular embodiments the dose administered is 0.4 mL to 0.8 mLs.

These and other aspects of the present invention will be better appreciated by reference to the following Detailed Description.

DETAILED DESCRIPTION OF THE INVENTION

The present invention provides efficacious, safe FCV vaccines. In particular embodiments the vaccine is nonadjuvanted. In one aspect, the vaccines of the present invention do not induce feline injection-site sarcomas, yet still aid in the protection of the vaccinates from the upper respiratory disease and/or limping syndrome caused by FCV infection. In a particular embodiment, the FCV capsid protein originates from a virulent systemic FCV (VS-FCV). In related embodiments, the FCV capsid protein originates from an older strain, such as an FCV F9 strain (F9-Like FCV).

Accordingly, the vaccine compositions of the present invention include an immunologically effective amount of a vector encoding an antigen from one or more strains of feline calicivirus that aids in eliciting protective immunity in the recipient vaccinated animal. Furthermore, the present invention provides new immunogenic compositions to improve the reliability of the vaccination to aid in the reduction of upper respiratory disease in cats in a feline infected by FCV and to thereby yield more transient or mild disease and/or lead to the reduction of the infection. In a particular aspect of the present invention, the vaccines comprise an alphavirus RNA replicon particle (RP) encoding an FCV capsid, e.g., originating from a VS-FCV or alternatively, a classical strain, such as an FCV F9-Like strain.

In more specific embodiments, the vaccines comprise alphavirus RNA replicon particles (RPs) that comprise the capsid protein and glycoproteins of Venezuelan Equine Encephalitis Virus (VEE) and encode the FCV capsid protein and/or an antigenic fragment thereof. In even more specific embodiments, the vaccines comprise alphavirus RNA replicon particles (RPs) that comprise the capsid protein and glycoproteins of the avirulent TC-83 strain of VEE and encode one or more FCV capsid proteins and/or one or more antigenic fragments thereof.

In another aspect of the present invention, the vaccines comprise naked DNA vectors that encode one or more FCV capsid proteins and/or one or more antigenic fragments thereof. The vaccines of the present invention can be administered to a feline in the absence of an adjuvant and still effectively aid in the protection of the vaccinated feline against FCV.

In order to more fully appreciate the invention, the following definitions are provided.

The use of singular terms for convenience in description is in no way intended to be so limiting. Thus, for example, reference to a composition comprising "a polypeptide" includes reference to one or more of such polypeptides. In addition, reference to an "alphavirus RNA replicon particle" includes reference to a plurality of such alphavirus RNA replicon particles, unless otherwise indicated.

As used herein the term "approximately" is used interchangeably with the term "about" and signifies that a value is within fifty percent of the indicated value i.e., a composition containing "approximately" $1\times10^8$ alphavirus RNA replicon particles per milliliter contains from $0.5\times10^8$ to $1.5\times10^8$ alphavirus RNA replicon particles per milliliter.

As used herein, the term "feline" refers to any member of the Felidae family. Domestic cats, pure-bred and/or mongrel companion cats, and wild or feral cats are all felines.

As used herein, the term "replicon" refers to a modified RNA viral genome that lacks one or more elements (e.g., coding sequences for structural proteins) that if they were present, would enable the successful propagation of the parental virus in cell cultures or animal hosts. In suitable cellular contexts, the replicon will amplify itself and may produce one or more sub-genomic RNA species.

As used herein, the term "alphavirus RNA replicon particle", abbreviated "RP", is an alphavirus-derived RNA replicon packaged in structural proteins, e.g., the capsid and glycoproteins, which also are derived from an alphavirus, e.g., as described by Pushko et al., [*Virology* 239(2):389-401 (1997)]. An RP cannot propagate in cell cultures or animal hosts (without a helper plasmid or analogous component), because the replicon does not encode the alphavirus structural components (e.g., capsid and glycoproteins).

The terms "FCV F9-Like" and "F9-Like FCV" are used interchangeably with each other and with the term "classical FCV" and as used herein is an FCV that can be characterized as an older and formerly, universal vaccine strain of FCV, for which the FCV F9 strain is considered a typical representative. In direct contrast, the FCV termed virulent systemic "VS-FCV" or as used herein interchangeably "(VS) FCV", is a newer class of FCV, which is unusually virulent, and cannot be neutralized by antibodies raised against the FCV F9-Like strains [see, U.S. Pat. No. 7,449,323; Radford et al., 38(2) Vet res. 319-335 (2007)].

The term "non-FCV", is used to modify terms such as pathogen, and/or antigen (or immunogen) to signify that the respective pathogen, and/or antigen (or immunogen) is neither an FCV pathogen nor an FCV antigen (or immunogen) and that a non-FCV protein antigen (or immunogen) does not originate from an FCV.

The terms "originate from", "originates from" and "originating from" are used interchangeably with respect to a given protein antigen and the pathogen or strain of that pathogen that naturally encodes it, and as used herein signify that the unmodified and/or truncated amino acid sequence of that given protein antigen is encoded by that pathogen or strain of that pathogen. The coding sequence, within a nucleic acid construct of the present invention for a protein antigen originating from a pathogen may have been genetically manipulated so as to result in a modification and/or truncation of the amino acid sequence of the expressed protein antigen relative to the corresponding sequence of that protein antigen in the pathogen or strain of pathogen (including naturally attenuated strains) it originates from.

As used herein, the terms "protecting", or "providing protection to", or "eliciting protective immunity to", "aids in prevention of disease", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, a "vaccine" is a composition that is suitable for application to an animal, e.g., feline (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a disease arising from an infection with a wild-type micro-organism, i.e., strong enough for aiding in the prevention of the disease, and/or preventing, ameliorating or curing the disease.

As used herein, a multivalent vaccine is a vaccine that comprises two or more different antigens. In a particular embodiment of this type, the multivalent vaccine stimulates the immune system of the recipient against two or more different pathogens.

The terms "adjuvant" and "immune stimulant" are used interchangeably herein, and are defined as one or more substances that cause stimulation of the immune system. In this context, an adjuvant is used to enhance an immune response to one or more vaccine antigens/isolates. Accordingly, "adjuvants" are agents that nonspecifically increase an immune response to a particular antigen, thus reducing the quantity of antigen necessary in any given vaccine, and/or the frequency of injection necessary in order to generate an adequate immune response to the antigen of interest. In this context, an adjuvant is used to enhance an immune response to one or more vaccine antigens/isolates. The American Association of Feline Practitioners Feline Vaccination Guidelines, for example, suggest the use of nonadjuvanted FeLV vaccines [AAFP Feline Advisory Panel, 15: 785-808 (2013)].

As used herein, a "nonadjuvanted vaccine" is a vaccine or a multivalent vaccine that does not contain an adjuvant.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient animal, e.g., feline.

Parenteral administration" includes subcutaneous injections, submucosal injections, intravenous injections, intramuscular injections, intradermal injections, and infusion.

As used herein the term "antigenic fragment" in regard to a particular protein (e.g., a protein antigen) is a fragment of that protein that is antigenic, i.e., capable of specifically interacting with an antigen recognition molecule of the immune system, such as an immunoglobulin (antibody) or T cell antigen receptor. For example, an antigenic fragment of an FCV capsid protein is a fragment of the capsid protein that is antigenic. In specific embodiments, the antigenic fragment of an FCV capsid protein comprises region E of the ORF2, which contains the major B-cell epitopes. Preferably, an antigenic fragment of the present invention is immunodominant for antibody and/or T cell receptor recognition. In particular embodiments, an antigenic fragment with respect to a given protein antigen is a fragment of that protein that retains at least 25% of the antigenicity of the full length protein. In preferred embodiments an antigenic fragment retains at least 50% of the antigenicity of the full length protein. In more preferred embodiments, an antigenic fragment retains at least 75% of the antigenicity of the full length protein. Antigenic fragments can be as small as 20 amino acids or at the other extreme, be large fragments that are missing as little as a single amino acid from the full-length protein. In particular embodiments the antigenic fragment comprises 25 to 150 amino acid residues. In other embodiments, the antigenic fragment comprises 50 to 250 amino acid residues. For FeLV, for example, the FeLV gp45 glycoprotein and the FeLV gp70 glycoprotein are antigenic fragments of the FeLV gp85 glycoprotein.

As used herein one amino acid sequence is 100% "identical" or has 100% "identity" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, MacVector (MacVector, Inc. Cary, N.C. 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein, the term "inactivated" microorganism is used interchangeably with the term "killed" microorganism. For the purposes of this invention, an "inactivated" microorganism is an organism which is capable of eliciting an immune response in an animal, but is not capable of infecting the animal. An antigen of the present invention (e.g., an inactivated feline calicivirus) may be inactivated by an agent selected from the group consisting of binary ethyleneimine, formalin, beta-propiolactone, thimerosal, or heat. In a particular embodiment, inactivated feline calicivirus isolates combined with an RP of the present invention are inactivated by binary ethyleneimine.

The alphavirus RNA replicon particles of the present invention may be lyophilized and rehydrated with a sterile water diluent. On the other hand, when the alphavirus RNA replicon particles are stored separately, but intended to be mixed with other vaccine components prior to administration, the alphavirus RNA replicon particles can be stored in the stabilizing solution of those components, e.g., a high sucrose solution.

A vaccine of the present invention can be readily administered by any standard route including intravenous, intramuscular, subcutaneous, oral, intranasal, intradermal, and/or intraperitoneal vaccination. The skilled artisan will appreciate that the vaccine composition is preferably formulated appropriately for each type of recipient animal and route of administration.

Thus, the present invention also provides methods of immunizing a feline against FCV and/or other feline pathogens. One such method comprises injecting a feline with an immunologically effective amount of a vaccine of the present invention, so that the feline produces appropriate FCV antibodies.

Multivalent Vaccines:

The present invention also provides multivalent vaccines. For example, the coding sequence of a protein antigen or antigenic fragment thereof, or combination of such coding sequences of protein antigens useful in a feline vaccine can be added to an alphavirus RNA replicon particle (RP) or combined in the same RP as one that encodes a feline antigen of the FCV [e.g., the FCV capsid protein] in the vaccine. In specific embodiments, the alphavirus RNA replicon particle encodes both the FCV F9-Like capsid protein or an antigenic fragment thereof and the VS-FCV capsid protein or an antigenic fragment thereof and encodes a non-FCV antigen. Accordingly, such multivalent vaccines are included in the present invention.

Examples of pathogens that one or more of such protein antigens can originate from include feline rhinotracheitis Virus (FVR), feline leukemia virus (FeLV), feline panleukopenia Virus (FPL) feline herpesvirus (FHV), other FCV strains, feline parvovirus (FPV), feline infectious peritonitis virus (FIPV), feline immunodeficiency virus, borna disease virus (BDV), rabies virus, feline influenza virus, canine influenza virus, avian influenza, canine pneumovirus, feline pneumovirus, *Chlamydophila felis* (FKA *Chlamydia psittaci*), *Bordetella bronchiseptica*, and *Bartonella* spp. (e.g., *B. henselae*). In particular embodiments, a coding sequence for a capsid protein or analogous protein from one or more of these feline or canine pathogens can be inserted into the same RP as the FCV antigen. Alternatively, or in combination therewith, a coding sequence for a capsid protein or analogous protein from one or more of these feline or canine pathogens can be inserted into one or more other RPs, which can be combined in a vaccine with an RP that encodes the FCV F9-Like capsid protein or an antigenic fragment thereof and/or the VS-FCV capsid protein or an antigenic fragment thereof.

In addition, an alphavirus RNA replicon particle (RP) that encodes one or more antigens of the FCV [e.g., the FCV F9-Like capsid protein or an antigenic fragment thereof and/or the VS-FCV capsid protein or an antigenic fragment thereof] can be added together with one or more other live, attenuated virus isolates, e.g., a live attenuated FCV F9-Like virus (e.g., modified live FCV F9) and/or a live attenuated feline herpesvirus and/or a live attenuated feline parvovirus and/or a live, attenuated feline leukemia virus, and/or a live, attenuated feline infectious peritonitis virus and/or a live, attenuated feline immunodeficiency virus and/or a live, attenuated borna disease virus and/or a live, attenuated rabies virus, and/or a live, attenuated feline influenza virus and/or a live, attenuated canine influenza virus, and/or a live, attenuated avian influenza, and/or a live, attenuated canine pneumovirus, and/or a live, attenuated feline pneumovirus. In addition, a live, attenuated *Chlamydophila felis*, and/or a live, attenuated *Bordetella bronchiseptica* and/or a live, attenuated *Bartonella* spp. (e.g., *B. henselae*) can also be included in such multivalent vaccines.

Furthermore, an alphavirus RNA replicon particle (RP) that encodes one or more antigens of the FCV [e.g., the FCV F9-Like capsid protein or an antigenic fragment thereof and/or the VS-FCV capsid protein or an antigenic fragment thereof] can be added together with one or more other killed virus isolates such as a killed FCV strain, and/or a killed feline herpesvirus and/or a killed feline parvovirus and/or a killed feline leukemia virus, and/or a killed feline infectious peritonitis virus and/or a killed feline immunodeficiency virus and/or a killed borna disease virus and/or a killed rabies virus, and/or a killed feline influenza virus and/or a killed canine influenza virus, and/or a killed avian influenza virus, and/or a killed canine pneumovirus, and/or a killed feline pneumovirus. In addition, bacterins (or subfractions of the bacterins, e.g., the pilus subfraction) of *Chlamydophila felis*, and/or *Bordetella bronchiseptica* and/or *Bartonella* spp. (e.g., *B. henselae*) can also be included in such multivalent vaccines.

It also is to be understood that this invention is not limited to the particular configurations, process steps, and materials disclosed herein as such configurations, process steps, and materials may vary somewhat. It further is to be understood that the terminology employed herein is used for the purpose of describing particular embodiments only and is not intended to be limiting, since the scope of the present invention will be limited only by the appended claims and equivalents thereof.

| SEQ ID NO: | Description | Type |
|---|---|---|
| 1 | Feline Calicivirus (VS-FCV) | nucleic acid DNA |
| 2 | Feline Calicivirus (VS-FCV) | amino acid |
| 3 | Feline Calicivirus (F9-like) | nucleic acid DNA |
| 4 | Feline Calicivirus (F9-like) | amino acid |
| 5 | FeLV viral glycoprotein (gp85) | nucleic acid DNA |
| 6 | FeLV viral glycoprotein (gp85) | amino acid |
| 7 | FeLV viral glycoprotein (gp70) | nucleic acid DNA |
| 8 | FeLV viral glycoprotein (gp70) | amino acid |
| 9 | Rabies virus Glycoprotein | nucleic acid DNA |
| 10 | Rabies virus Glycoprotein | amino acid |
| 11 | GGCGCGCCGCACC | nucleic acid |
| 12 | Feline Calicivirus (VS-FCV) | nucleic acid RNA |
| 13 | Feline Calicivirus (F9-like) | nucleic acid RNA |
| 14 | FeLV viral glycoprotein (gp85) | nucleic acid RNA |
| 15 | FeLV viral glycoprotein (gp70) | nucleic acid RNA |
| 16 | Rabies virus Glycoprotein | nucleic acid RNA |
| | TTAATTAA | nucleic acid |

SEQUENCES
Feline Calicivirus capsid (VS-FCV)

SEQ ID NO: 1 atggctgacgacggatctgtgaccaccccagaacaaggaacaatggtcggaggagtgatt gccgaacccagcgctcagatgtcaactgcggcggacatggcctccggaaagtcggtggac tccgagtgggaagccttcttctcgttccacacgtccgtgaactggagcacctccgaaacc caaggaaagatcctcttcaagcagtccctgggtcccctgctgaacccgtacctggagcac atcagcaagctgtacgtcgcttggagcgggtcgatcgaagtgcgattttccatctcggga agcggcgtgttcggtggtaaactggccgccatcgtcgtgccgcctggtgtcgaccctgtc cagtcaacctccatgctgcagtacccgcacgtcctgttcgacgcaagacaagtggagcca gtgatcttctccatcccggacctccgcaacagcctgtatcacttgatgtccgataccgat accacttccctcgtgatcatggtgtacaacgatctgatcaacccgtacgccaatgactcc aacagctcgggttgcatcgtgaccgtcgaaacgaagcctggcatcgatttcaagtttcat ctgctgaaaccgcccggatccatgcttactcacgggtccatcccttccgatctgatcccc aagagctcctccctgtggattgggaaccgccactggaccgatattaccgatttcgtgatt cggcctttcgtgttccaagccaaccggcacttcgacttcaaccaggagactgccggctgg tcaactccacggttccgcccattggccgtgactgtgtcgcagtcaaagggagccaagctc gggaacggcatcgccaccgactacattgtgcctggaatccccgacggatggcctgatact accatccccaccaagctgacccctaccggagattacgccatcacctcctccgacggcaat gatattgaaaccaagctggaatacgagaacgcggacgtgattaagaacaacaccaacttc cgctccatgtatatctgcggaagcctccagagggcttggggcgacaagaagatcagcaac accgggttcatcactaccggagtgatttctgacaactccatcagcccttcgaacacaatt gaccagtccaagatcgtggtgtaccaggacaaccatgtcaattcggaggtccagactagc gacatcactcttgccatcctgggctacaccggaattggagaagaggccataggcgccaac cgggactccgtcgtgagaatttccgtgcttccggaaactggagcaaggggcggaaatcac cccatcttctacaaaaattccatgaagctgggctacgtgatctcctccattgacgtgttc -continued aactcccaaatcctccacacctcgcgccagctgtcactgaacaactacttgttgcccct gactccttcgcggtgtaccggattattgacagcaacggatcatggttcgacattgggatt gacagcgatgggttttcattcgtgggcgtgtcgtcatttccaaagctggagtttccgctg tccgcctcatacatgggcatccagctcgcaaagatccggctggcgtccaacatccggtca tccatgactaagctgtga Feline Calicivirus capsid (VS-FCV)

SEQ ID NO: 2

MADDGSVTTPEQGTMVGGVIAEPSAQMSTAADMASGKSVDSEWEAFFSFHTSVNWSTSET

QGKILFKQSLGPLLNPYLEHISKLYVAWSGSIEVRFSISGSGVFGGKLAAIWPPGVDPV

QSTSMLQYPHVLFDARQVEPVIFSIPDLRNSLYHLMSDTDTTSLVIMVYNDLINPYANDS

NSSGCIVTVETKPGIDFKFHLLKPPGSMLTHGSIPSDLIPKSSSLWIGNRHWTDITDFVI

RPFVFQANRHFDFNQETAGWSTPRFRPLAVTVSQSKGAKLGNGIATDYIVPGIPDGWPDT

TIPTKLTPTGDYAITSSDGNDIETKLEYENADVIKNNTNFRSMYICGSLQRAWGDKKISN

TGFITTGVISDNSISPSNTIDQSKIWYQDNHVNSEVQTSDITLAILGYTGIGEEAIGAN

RDSWRISVLPETGARGGNHPIFYKNSMKLGYVISSIDVFNSQILHTSRQLSLNNYLLPP

DSFAVYRIIDSNGSWFDIGIDSDGFSFVGVSSFPKLEFPLSASYMGIQLAKIRLASNIRS

SMTKL

Feline Calicivirus (VS-FCV) capsid (SEQ ID NO: 12)

auggcugacgacggaucugugaccaccccagaacaaggaacaauggucggaggagugauu gccgaacccagcgcucagaugucaacugcggcggacauggccuccggaaagucgguggac uccgagugggaagccuucuucucguuccacacguccgugaacuggagcaccuccgaaacc caaggaaagauccucuucaagcagucccugggucccugcugaacccguaccuggagcac aucagcaagcuguacgucgcuuggagcgggucgaucgaagugcgauuuuccaucucggga agcggcguguucgguggua aacuggccgccaucgucgugccgccuggugucgacccuguc cagucaaccuccaugcugcaguacccgcacguccuguucgacgcaagacaaguggagcca gugaucuucuccaucccggaccuccgcaacagccuguaucacuugauguccgauaccgau accacuucccucgugaucaugguguacaacgaucugaucaacccguacgccaaugacucc aacagcucggguugcaucgugaccgucgaaacgaagccuggcaucgauuucaaguuucau cugcugaaaccgcccggauccaugcuuacucacggguccaucccuuccgaucugaucccc aagagcuccucccuguggauugggaaccgccacuggaccgauauuaccgauuucgugauu cggccuuucguguuccaagccaaccggcacuucgacuucaaccaggagacugccggcugg ucaacuccacgguuccgcccauuggccgugacugugucgcagucaaagggagccaagcuc gggaacggcaucgccaccgacuacauugugccuggaauccccgacggauggccugauacu accaucccaccaagcugaccccuaccggagauuacgccaucaccuccuccgacggcaau gauauugaaaccaagcuggaauacgagaacgcggacgugauuaagaacaacaccaacuuc cgcuccauguauaucugcggaagccuccagagggcuuggggcgacaagaagaucagcaac accggguucaucacuaccggagugauuucugacaacuccaucagcccuucgaacacaauu gaccaguccaagaucgugguguaccaggacaaccaugucaauucggagguccagacuagc gacaucacucuugccauccugggcuacaccggaauuggagaagaggccauaggcgccaac cgggacuccgucgugagaauuuccgugcuuccggaaacuggagcaaggggcggaaaucac cccaucuucuacaaaaauuccaugaagcugggcuacgugaucuccuccauugacguguuc -continued aacucccaaauccuccacaccucgcgccagcugucacugaacaacuacuuguugcccccu gacuccuucgcgguguaccggauuauugacagcaacggaucaugguucgacauugggauu gacagcgauggguuuucauucgugggcgugucgucauuuccaaagcuggaguuuccgcug uccgccucauacaugggcauccagcucgcaaagaucccggcuggcguccaacauccgguca uccaugacuaagcuguga Feline Calicivirus (F9-like) capsid (SEQ ID NO: 3)

atgactgccccggaacaaggaacgatggtcggaggagtgattgcagaaccgtcagcacag atgtccaccgctgccgacatggccactggaaagagcgtggactccgaatgggaagccttc ttctccttccacacttcggtcaactggtcgactagcgaaacccaggggaagattttgttc aagcaatccctcggccctctgctgaacccctacctggagcatctggccaagctgtacgtg gcatggtcgggcagcatcgaagtgcgctttagcatttccggctccggagtgttcgggggga aagcttgctgccattgtcgtgccgccaggagtggacccggtgcagtccacttctatgctc caatacccgcatgtcctgttcgacgccagacaggtggagcctgtgatcttttgcctgccg gatctcaggtccaccctgtatcacctcatgtccgacaccgacaccacctcgctcgtgatc atggtgtacaacgacctgatcaacccctacgctaacgacgccaacagctcaggttgcatt gtgactgtcgaaaccaagccaggccctgacttcaagtttcatttgctgaagccgcccggt tccatgctgacccacggctcgatcccatccgacctgatccccaagacgagctccctgtgg atcggaaaccgctactggtccgatattaccgacttcgtgatcagaccattcgtgttccaa gccaaccgccatttcgacttcaaccaggaaaccgcaggatggtcgacccctcgattccgc ccgatttcagtgaccatcaccgaacagaacggcgcgaagctgggaattggcgtggcgacc gactacatcgtgccgggaatcccggatggatggcctgatacgaccattcccggggagctg atccctgccggggactacgccatcaccaacggtactggaaacgacatcaccactgccacc ggttacgacaccgccgacatcataaagaacaacaccaacttcagaggaatgtacatttgc ggctccctgcaacgcgcttggggtgacaaaaagatctcgaacactgccttcatcacaaca gcgactctggacggcgataacaacaacaagatcaatccttgtaataccatcgaccagtcc aaaatcgtggtgttccaggataaccacgtgggaaagaaggcgcagacctccgacgacact ctggcgctgcttggctacaccgggatcggcgagcaggccattggaagcgatcggatcgg gtcgtgcggatctccaccctccccgagactggagcaaggggaggcaaccaccccatcttt tacaaaaaacagcattaagctcggatacgtcatccgctccatcgatgtgttcaactctcaa atcctgcacacttcgcggcagctgtccctgaaccactacctcttgccgcccgactccttc gccgtctaccggatcattgattcgaacgggagctggttcgacatcggcattgatagcgat ggcttctcgtttgtgggcgtgtcgggcttcgggaagctggagttccccactgagcgcctca tacatgggtatccagctggccaagatcaggctggcctccaacatccgctcacctatgact aagctgtga Feline Calicivirus (F9-like) capsid (SEQ ID NO: 4)

MTAPEQGTMVGGVIAEPSAQMSTAADMATGKSVDSEWEAFFSFHTSVNWSTSETQGKILF

KQSLGPLLNPYLEHLAKLYVAWSGSIEVRFSISGSGVFGGKLAAIWPPGVDPVQSTSML

QYPHVLFDAPQVEPVIFCLPDLRSTLYHLMSDTDTTSLVIMVYNDLINPYANDANSSGCI

VTVETKPGPDFKFHLLKPPGSMLTHGSIPSDLIPKTSSLWIGNRYWSDITDFVIRPFVFQ

ANRHFDFNQETAGWSTPRFRPISVTITEQNGAKLGIGVATDYIVPGIPDGWPDTTIPGEL

IPAGDYAITNGTGNDITTATGYDTADIIKNNTNFRGMYICGSLQRAWGDKKISNTAFITT

-continued

ATLDGDNNNKINPCNTIDQSKIWFQDNHVGKKAQTSDDTLALLGYTGIGEQAIGSDRDR

WRISTLPETGARGGNHPIFYKNSIKLGYVIRSIDVFNSQILHTSRQLSLNHYLLPPDSF

AVYRIIDSNGSWFDIGIDSDGFSFVGVSGFGKLEFPLSASYMGIQLAKIRLASNIRSPMT

KL

Feline Calicivirus (F9-like) capsid (SEQ ID NO: 13)

augacugccccggaacaaggaacgauggucggaggagugauugcagaaccgucagcacag auguccaccgcugccgacauggccacuggaaagagcguggacuccgaaugggaagccuuc uucuccuuccacacuucggucaacuggucgacuagcgaaacccaggggaagauuuuguuc aagcaaucccucggcccucugcugaaccccuaccuggagcaucuggccaagcuguacgug gcauggucgggcagcaucgaagugcgcuuuagcauuuccggcuccggagguguucgggga aagcuugcugccauugucgugccgccaggaguggacccggugcaguccacuucuaugcuc caauacccgcauguccuguucgacgccagacagguggagccugugaucuuuugccugccg gaucucagguccacccuguaucaccucauguccgacaccgacaccaccucgcucgugauc augguguacaacgaccugaucaaccccuacgcuaacgacgccaacagcucagguugcauu gugacugucgaaaccaagccaggcccugacuucaaguuucauuugcugaagccgcccggu uccaugcugacccacggcucgaucccauccgaccugauccccaagacgagcucccugugg aucggaaaccgcuacugguccgauauuaccgacuucgugaucagaccauucguguuccaa gccaaccgccauuucgacuucaaccaggaaaccgcaggauggucgaccccucgauuccgc ccgauuucagugaccaucaccgaacagaacggcgcgaagcugggaauuggcguggcgacc gacuacaucgugccgggaaucccggauggauggccugauacgaccauucccggggagcug aucccugccggggacuacgccaucaccaacgguacuggaaacgacaucaccacugccacc gguuacgacaccgccgacaucauaaagaacaacaccaacuucagaggaauguacauuugc ggcucccugcaacgcgcuuggggugacaaaaagaucucgaacacugccuucaucacaaca gcgacucuggacggcgauaacaacaacaagaucaauccuuguaauaccaucgaccagucc aaaaucgugguguuccaggauaaccacgugggaaagaaggcgcagaccuccgacgacacu cuggcgcugcuuggcuacaccgggaucggcgagcaggccauuggaagcgaucggaucgg gucgugcggaucuccacccucccgagacuggagcaaggggaggcaaccaccccaucuuu uacaaaaacagcauuaagcucggauacgucauccgcuccaucgauguguucaacucucaa auccugcacacuucgcggcagcugucccugaaccacuaccucuugccgcccgacuccuuc gccgucuaccggaucauugauucgaacgggagcugguucgacaucggcauugauagcgau ggcuucucguuugugggcgugucgggcuucgggaagcuggaguucccacugagcgccuca uacauggguauccagcuggccaagaucaggcuggccuccaacauccgcucaccuaugacu aagcuguga Feline Leukemia Virus envelope glycoprotein (gp85)

SEQ ID NO: 5 atggagtcaccaacacaccctaaaccttctaaagacaaaaccctctcgtggaatctcgccttccttgt gggcatcctgttcacaatcgacatcggcatggccaaccccttcgccgcatcagatctacaatgtgacat gggtcattactaatgtgcagacaaacacccaggcaaatgctacttctatgcttggtactctgactgat gcttatccaaccctgcacgtcgacctttgcgatctcgtcggtgacacatgggagcccatcgtgctgaa tccaactaatgtcaaacatggtgccaggtattcttctagcaaatacgggtgtaagaccactgatcgga agaaacagcaacaaacctacccattctacgtgtgcccgggtcacgcaccgtccctgggtccgaaggga -continued acacattgtgggggagcccaagacggtttttgcgctgcttggggttgtgaaacaaccggagaagcctg gtggaagcctacctcatcttgggactacattactgtgaaaagaggctctagccaggataacagctgcg aaggaaagtgtaatcccctggtgcttcaattcacccagaaaggccggcaggcatcatgggatggaccg aaaatgtggggacttagactctatcgcaccggatacgaccccatcgctctgtttactgtgtcacgcca agtctccaccattactccgccacaggccatggggccgaatctggtcctccccgatcagaagccaccct cacggcaaagtcaaaccggctcaaaagtggccacccaacggccccagacaaatgagtccgcacctagg tcagtggcacctacaacaatgggtccaaagcggatcggaaccggagacaggctcattaacctcgtgca agggacttatctggcccttaacgctactgaccccaacaagaccaaggattgctggctctgccttgtga gcagacctccttactatgaggggatcgccattctcggaaactactcaaatcagaccaaccccccctccg tcgtgtctgagcacccccccagcacaagcttactatttcagaagtcagtggacagggaatgtgcatcgg aaccgtgccaaagactcatcaagccctttgcaacaaaactcaacaagggcacactggagctcattatc tcgccgcacctaacgggacctactgggcttgcaatactggattgaccccgtgtatctctatggccgtg ctgaattggacttccgacttctgcgtgcttattgagctttggcctagagtgacataccatcagcctga gtacgtctatacccatttcgccaaggcagtcagattccggcgggagcctatctccctgactgtggcct tgatgctcggtggactgacagtgggaggaattgcagctggagtcggaactggaaccaaggccctgctc gaaactgctcagttccggcagctgcagatggccatgcacactgacatccaggctctggaggaatcaat ttcagcccttgagaaaagcttgacctcgctgtctgaagtggtcctccaaaacaggcgcggtttggaca tcctgttccttcaagagggtggtctgtgcgccgctctcaaggaggaatgctgtttctacgctgaccat accgggctggtgcgcgataacatggcaaagctgcgggaacgcttgaaacagaggcagcaactgttcga ctctcagcagggatggttcgagggctggtttaacaagagcccatggtttaccactctgatctcttcaa tcatgggtccactgctcatcctgcttctgattcttctcttcggaccgtgtattctcaacaggctggtg cagtttgtcaaggacagaatctcggtggtccaggccctgattcttactcagcagtatcagcagattaa gcagtacgaccccgatcggccttga Feline Leukemia Virus envelope glycoprotein (gp85)

SEQ ID NO: 6

MESPTHPKPSKDKTLSWNLAFLVGILFTIDIGMANPSPHQIYNVTWVITNVQTNTQANAT

SMLGTLTDAYPTLHVDLCDLVGDTWEPIVLNPTNVKHGARYSSSKYGCKTTDRKKQQQTY

PFYVCPGHAPSLGPKGTHCGGAQCGFCAAWGCETTGEAWWKPTSSWDYITVKRGSSQDNS

CEGKCNPLVLQFTQKGRQASWDGPKMWGLRLYRTGYDPIALFTVSRQVSTITPPQAMGPN

LVLPDQKPPSRQSQTGSKVATQRPQTNESAPRSVAPTTMGPKRIGTGDRLINLVQGTYLA

LNATDPNKTKDCWLCLVSRPPYYEGIAILGNYSNQTNPPPSCLSTPQHKLTISEVSGQGM

CIGTVPKTHQALCNKTQQGHTGAHYLAAPNGTYWACNTGLTPCISMAVLNWTSDFCVLIE

LWPRVTYHQPEYVYTHFAKAVRFRREPISLTVALMLGGLTVGGIAAGVGTGTKALLETAQ

FRQLQMAMHTDIQALEESISALEKSLTSLSEWLQNRRGLDILFLQEGGLCAALKEECCF

YADHTGLVRDNMAKLRERLKQRQQLFDSQQGWFEGWFNKSPWFTTLISSIMGPLLILLLI

LLFGPCILNRLVQFVKDRISWQALILTQQYQQIKQYDPDRP*

Feline Leukemia Virus envelope glycoprotein (gp85)

SEQ ID NO: 14 auggagucaccaacacacccuaaaccuucuaaagacaaaacccucucguggaaucucgccuuccuugu gggcauccuguucacaaucgacaucggcauggccaacccuucgccgcaucagaucuacaaugugacau gggucauuacuaaugugcagacaaacacccaggcaaaugcuacuucuaugcuugguacucugacugau gcuuauccaacccugcacgucgaccuuugcgaucucgucggugacacaugggagcccaucgugcugaa uccaacuaaugucaaacaugguguccagguauucuucuagcaaauacggguguaagaccacugaucgga -continued agaaacagcaacaaaccuacccauucuacgugugcccgggucacgcaccgucccuggguccgaaggga acacauugugggggagcccaagacgguuuuugcgcugcuugggguugugaaacaaccggagaagccug guggaagccuaccucaucuugggacuacauuacugugaaaagaggcucuagccaggauaacagcugcg aaggaaaguguaauccccuggugcuucaauucacccagaaaggccggcaggcaucaugggauggaccg aaaauguggggacuuagacucuaucgcaccggauacgaccccaucgcucuguuuacugugucacgcca agucuccaccauuacuccgccacaggccauggggccgaaucugguccuccccgaucagaagccacccu cacggcaaagucaaaccggcucaaaaguggccacccaacggccccagacaaaugaguccgcaccuagg ucaguggcaccuacaacaaugggucccaaagcggaucggaaccggagacaggcucauuaaccucgugca agggacuuaucuggcccuuaacgcuacugaccccaacaagaccaaggauugcuggcucugccuuguga gcagaccuccuuacuaugaggggaucgccauucucggaaacuacucaaaucagaccaaccccccuccg ucgugucugagcacccccccagcacaagcuuacuauuucagaagucaguggacagggaaugugcaucgg aaccgugccaaagacucaucaagcccuuugcaacaaaacucaacaagggcacacuggagcucauuauc ucgccgcaccuaacgggaccuacugggcuugcaauacuggauugaccccguguaucucuauggccgug cugaauuggacuuccgacuucugcgugcuuauugagcuuuggccuagagugacauaccaucagccuga guacgucuauacccauuucgccaaggcagucagauuccggcgggagccuaucucccugacuguggccu ugaugcucgguggacugacagugggaggaauugcagcuggagucggaacuggaaccaaggcccugcuc gaaacugcucaguuccggcagcugcagauggccaugcacacugacauccaggcucuggaggaaucaau uucagcccuugagaaaagcuugaccucgcugucugaaguggucuccaaaacaggcgcgguuuggaca uccuguuccuucaagaggguggucugugcgccgcucucaaggaggaaugcuguuucuacgcugaccau accgggcuggugcgcgauaacauggcaaagcugcgggaacgcuugaaacagaggcagcaacuguucga cucucagcagggaugguucgagggcugguuuaacaagagcccaugguuuaccacucugaucucuucaa ucaugggucccacugcucauccugcuucugauucuucucuucggaccguguauucucaacaggcuggug caguuugucaaggacagaaucucgguggucccaggcccugauucuuacucagcaguaucagcagauuaa gcaguacgaccccgaucggccuuga Feline Leukemia Virus envelope glycoprotein (gp70)

SEQ ID NO: 7 aatcctagtccacaccaaatatataatgtaacttgggtaataaccaatgtacaaactaacacc caagctaacgccacctctatgttaggaaccttaaccgatgcctaccctaccctacatgttgac ttatgtgacctagtgggagacacctgggaacctatagtcctaaacccaaccaatgtaaaacac ggggcacgttactcctcctcaaaatatggatgtaaaactacagatagaaaaaaacagcaacag acataccccttttacgtctgccccggacatgccccctcgttggggccaaagggaacacattgt ggaggggcacaagatgggttttgtgccgcatggggatgtgagaccaccggagaagcttggtgg aagcccacctcctcatgggactatatcacagtaaaaagagggagtagtcaggacaatagctgt gagggaaaatgcaacccccctggttttgcagttcacccagaagggaagacaagcctcttgggac ggacctaagatgtggggattgcgactataccgtacaggatatgaccctatcgctttattcacg gtgtcccggcaggtatcaaccattacgccgcctcaggcaatgggaccaaacctagtcttacct gatcaaaaacccccatcccgacaatctcaaacagggtccaaagtggcgacccagaggccccaa acgaatgaaagcgccccaaggtctgttgcccccaccaccatgggtcccaaacggattgggacc ggagataggttaataaatttagtacaagggacatacctagccttaaatgccaccgaccccaac aaaactaaagactgttggctctgcctggtttctcgaccaccctattacgaagggattgcaatc ttaggtaactacagcaaccaaacaaaccccccccatcctgcctatctactccgcaacacaaa -continued ctaactatatctgaagtatcagggcaaggaatgtgcatagggactgttcctaaaacccaccag gctttgtgcaataagacacaacagggacatacaggggcgcactatctagccgcccccaacggc acctattgggcctgtaacactggactcaccccatgcatttccatggcggtgctcaattggacc tctgatttttgtgtcttaatcgaattatggcccagagtgacttaccatcaacccgaatatgtg tacacacattttgccaaagctgtcaggttccgaaga Feline Leukemia Virus envelope glycoprotein (gp70)

SEQ ID NO: 8

NPSPHQIYNVTWVITNVQTNTQANATSMLGTLTDAYPTLHVDLCDLVGDTWEPIVLNPTNVKH16850866

KYGCKTTDRKKQQQTYPFYVCPGHAPSLGPKGTHCGGAQDGFCAAWGCETTGEAWWKPTSSWDYITVKRG

SSQDNSCEGKCNPLVLQFTQKGRQASWDGPKMWGLRLYRTGYDPIALFTVSRQVSTITPPQAMGPNLVLP

DQKPPSRQSQTGSKVATQRPQTNESAPRSVAPTTMGPKRIGTGDRLINLVQGTYLALNATDPNKTKDCWL

CLVSRPPYYEGIAILGNYSNQTNPPPSCLSTPQHKLTISEVSGQGMCIGTVPKTHQALCNKTQQGHTGAH

YLAAPNGTYWACNTGLTPCISMAVLNWTSDFCVLIELWPRVTYHQPEYVYTHFAKAVRFRR

Feline Leukemia Virus envelope glycoprotein (gp70)

SEQ ID NO: 15 aauccuaguccacaccaaauauauaauguaacuuggguaauaaccaauguacaaacuaacacc caagcuaacgccaccucuauguuaggaaccuuaaccgaugccuacccuacccuacauguugac uuaugugaccuagugggagacaccugggaaccuauaguccuaaacccaaccaauguaaaacac ggggcacguuacuccuccucaaaauauggauguaaaacuacagauagaaaaaaacagcaacag acauaccccuuuuacgucugccccggacaugccccucguuggggccaaagggaacacauugu ggaggggcacaagaugggguuuugugccgcauggggaugugagaccaccggagaagcuuggugg aagcccaccuccucaugggacuauaucacaguaaaaagagggaguagucaggacaauagcugu gagggaaaaugcaaccccccugguuuugcaguucacccagaagggaagacaagccucuugggac ggaccuaagaugugggauugcgacuauaccguacaggauaugacccuaucgcuuuauucacg gugucccggcagguaucaaccauuacgccgccucaggcaaugggaccaaaccuagucuuaccu gaucaaaaacccccaucccgacaaucucaaacaggguccaaaguggcgacccagaggccccaa acgaaugaaagcgccccaaggucuguugcccccaccaccaugggucccaaacggauugggacc ggagauagguuaauaaauuuaguacaagggacauaccuagccuuaaaugccaccgaccccaac aaaacuaaagacuguuggcucugccugguuucucgaccacccuauuacgaagggauugcaauc uuagguaacuacagcaaccaaacaaaccccccccauccugccuaucuacuccgcaacacaaa cuaacuauaucugaaguaucagggcaaggaaugugcauagggacuguuccuaaaacccaccag gcuuugugcaauaagacacaacagggacauacaggggcgcacuaucuagccgcccccaacggc accuauugggccuguaacacuggacucaccccaugcauuuccauggcggugcucaauuggacc ucugauuuuugugucuuaaucgaauuauggcccagagugacuuaccaucaacccgaauaugug uacacacauuuugccaaagcugucagguuccgaaga

RABIES VIRUS G (SEQ ID NO: 9)

atggtgccgcaggctctcctgtttgtccccttctggtctttccattgtgttttgggaaattccctat ctacacaattccggacaagttgggaccctggagcccaattgacattcatcatctcagctgcccgaaca atttggtcgtggaggacgaaggatgcaccaacctgtcggggttctcctacatggaattgaaagtcgga tacatcagtgccattaagatgaacgggttcacttgcacaggcgtcgtgactgaagctgagacatacac taacttcgtgggatatgtcactaccactttcaaaagaaagcatttccgccctactcctgatgcttgta gggccgcatacaactggaagatggccggtgaccccagatatgaggaatcacttcacaatccgtaccct gactaccactggcttcggactgtcaaaaccaccaaggagtcactcgtgatcattagtccaagtgtggc -continued tgatcttgacccatacgaccggtcacttcactcacgggtgttcccgggggggaattgctctggtgtcg
cagtgtcgtcaacctactgctccacaaaccacgattacaccatttggatgccagaaaatcctcggctt
ggtatgtcatgtgacattttcaccaattctcgggggaagagggcttccaaagggtctgaaacttgcgg
ctttgtcgatgagcggggcttgtataagtcacttaaaggtgcttgcaaactcaagctttgtggtgtct
tgggattgagattgatggatggaacttgggtcgcaatgcagacttctaacgaaaccaaatggtgccct
cccggacagcttgtgaatttgcatgactttcgctctgacgaaattgagcatcttgtcgtcgaggagtt
ggtcaagaagcgggaagagtgtctggatgctttggaatcaatcatgaccaccaagtcagtgtctttca
gacggctctcacatcttaggaaattggtgccaggttttggaaaagcatataccattttcaacaagacc
cttatggaagccgatgctcactacaagtctgtcaggacttggaatgagatcatcccgtctaaagggtg
tcttagggtcggagggagatgtcatcctcatgtcaacggagtctttttcaatggtatcattcttggac
ctgacggaaatgtccttatccctgagatgcaatcttccctcctccagcaacacatggaacttcttgtc
tcatcggtcatccccctttatgcacccccctggctgacccatcaaccgtgttcaagaacggtgacgaggc
agaggattttgtcgaggtccaccttcccgatgtgcatgaacggatctctggtgtcgaccttggactcc
ctaac tggggaaagtatgtccttctgtcggcaggagccctgactgccttgatgttgattatcttcct
gatgacttgttggaggagagtcaatcggtcggagccaacacaacataatctcagaggaacaggaaggg
aggtgtcagtcacaccccaaagcgggaagatcatttcgtcttgggagtcatacaagagcggaggtgaa
accggactgtga

RABIES VIRUS G (SEQ ID NO: 10)

MVPQALLFVPLLVFPLCFGKFPIYTIPDKLGPWSPIDIHHLSCPNNLWEDEGCTNLSGF
SYMELKVGYISAIKMNGFTCTGWTEAETYTNFVGYVTTTFKRKHFRPTPDACRAAYNWK
MAGDPRYEESLHNPYPDYHWLRTVKTTKESLVIISPSVADLDPYDRSLHSRVFPGGNCSG
VAVSSTYCSTNHDYTIWMPENPRLGMSCDIFTNSRGKRASKGSETCGFVDERGLYKSLKG
ACKLKLCGVLGLRLMDGTWVAMQTSNETKWCPPGQLVNLHDFRSDEIEHLWEELVKKRE
ECLDALESIMTTKSVSFRRLSHLRKLVPGFGKAYTIFNKTLMEADAHYKSVRTWNEIIPS
KGCLRVGGRCHPHVNGVFFNGIILGPDGNVLIPEMQSSLLQQHMELLVSSVIPLMHPLAD
PSTVFKNGDEAEDFVEVHLPDVHERISGVDLGLPNWGKYVLLSAGALTALMLIIFLMTCW
RRVNRSEPTQHNLRGTGREVSVTPQSGKIISSWESYKSGGETGL*

RABIES VIRUS G (SEQ ID NO: 16)

auggugccgcaggcucuccuguuuguccccuucuggucuuuccauuguguuugggaaauucccuauc
uacacaauuccggacaaguugggacccuggagcccaauugacauucaucaucucagcugcccgaacaau
uuggucguggaggacgaaggaugcaccaaccugucgggguucuccuacauggaauugaaagucggauac
aucagugccauuaagaugaacggguucacuugcacaggcgucgugacugaagcugagacauacacuaac
uucgugggauaugucacuaccacuuucaaaagaaagcauuuccgcccuacuccugaugcuuguagggcc
gcauacaacuggaagauggccggugaccccagauaugaggaaucacuucacaauccguacccugacuac
cacuggcuucggacugucaaaaccaccaaggagucacucgugaucauuaguccaaguguggcugaucuu
gacccauacgaccggucacuucacucacggguguucccgggggggaauugcucuggugucgcagugucg
ucaaccuacugcuccacaaaccacgauuacaccauuuggaugccagaaaauccucggcuugguauguca
ugugacauuuucaccaauucucgggggaagagggcuuccaaagggucugaaacuugcggcuuugucgau
gagcggggcuuguauaagucacuuaaaggugcuugcaaacucaagcuuuguggugucuugggauugaga
uugauggauggaacuugggucgcaaugcagacuucuaacgaaaccaaauggugcccucccggacagcuu -continued

```
gugaauuugcaugacuuucgcucugacgaaauugagcaucuugucgucgaggaguuggucaagaagcgg

gaagagugucuggaugcuuuggaaucaaucaugaccaccaagucagugucuuucagacggcucucacau

cuuaggaaauuggugccagguuuuggaaaagcauauaccauuuucaacaagacccuuauggaagccgau

gcucacuacaagucugucaggacuuggaaugagaucaucccgucuaaagggugucuuagggucggaggg

agaugucauccucaugucaacggagucuuuuucaaugguaucauucuuggaccugacggaaauguccuu

aucccugagaugcaaucuucccuccuccagcaacacauggaacuucuugucucaucggucaucccccuu

augcacccccuggcugacccaucaaccguguucaagaacggugacgaggcagaggauuuugucgagguc

caccuucccgaugugcaugaacggaucucuggugucgaccuuggacucccuaacuggggaaaguauguc

cuucugucggcaggagcccugacugccuugauguugauuaucuuccugaugacuuguuggaggagaguc

aaucggucggagccaacacaacauaaucucagaggaacaggaagggaggugucagucacaccccaaag

cgggaagaucauuucgucuugggagucauacaagagcggaggugaaaccggacuguga
```

The following examples serve to provide further appreciation of the invention but are not meant in any way to restrict the effective scope of the invention.

EXAMPLES

Example 1

Incorporation of the Coding Sequences for FCV Capsid Proteins into the Alphavirus RNA Replicon Particles

Introduction

RNA viruses have been used as vector-vehicles for introducing vaccine antigens, which have been genetically engineered into their genomes. However, their use to date has been limited primarily to incorporating viral antigens into the RNA virus and then introducing the virus into a recipient host. The result is the induction of protective antibodies against the incorporated viral antigens. Alphavirus RNA replicon particles have been used to encode pathogenic antigens. Such alphavirus replicon platforms have been developed from several different alphaviruses, including Venezuelan equine encephalitis virus (VEE) [Pushko et al., *Virology* 239:389-401 (1997)], Sindbis (SIN) [Bredenbeek et al., *Journal of Virology* 67:6439-6446 (1993) the contents of which are hereby incorporated herein in their entireties], and Semliki Forest virus (SFV) [Liljestrom and Garoff, *Biotechnology* (NY) 9:1356-1361 (1991), the contents of which are hereby incorporated herein in their entireties]. Moreover, alphavirus RNA replicon particles are the basis for several USDA-licensed vaccines for swine and poultry. These include: Porcine Epidemic Diarrhea Vaccine, RNA Particle (Product Code 19U5.P1), Swine Influenza Vaccine, RNA (Product Code 19A5.D0), Avian Influenza Vaccine, RNA (Product Code 1905.D0), and Prescription Product, RNA Particle (Product Code 9PP0.00).

Alphavirus RNA Replicon Particle Construction

Amino acid sequences for FCV capsid proteins were used to generate codon-optimized (feline codon usage) nucleotide sequences in silico. Optimized sequences were prepared as synthetic DNA by a commercial vendor (ATUM, Newark, Calif.). Accordingly, synthetic genes were designed based on the amino acid sequences of a VS-FCV capsid protein and an FCV F9-like capsid protein, respectively. The constructs that encode the amino acid sequence for the VS-FCV capsid protein [SEQ ID NO: 2], or for the FCV F9-like capsid protein [SEQ ID NO: 4], were codon-optimized for feline, with flanking sequence appropriate for cloning into the alphavirus replicon plasmid.

The VEE replicon vectors designed to express FCV capsid proteins were constructed as previously described [see, U.S. Pat. No. 9,441,247 B2; the contents of which are hereby incorporated herein by reference], with the following modifications. The TC-83-derived replicon vector "pVEK" [disclosed and described in U.S. Pat. No. 9,441,247 B2] was digested with restriction enzymes AscI and PacI. A DNA plasmid containing the codon-optimized open reading frame nucleotide sequence of one of the FCV capsid protein genes (either FCV F9-Like or VS-FCV), with 5' flanking sequence (5'-GGCGCGCCGCACC-3') [SEQ ID NO: 11] and 3' flanking sequence (5'-TTAATTAA-3'), were similarly digested with restriction enzymes AscI and PacI. The synthetic gene cassette was then ligated into the similarly digested pVEK vector, and the resulting clones were re-named "pVHV-F9" and "pVHV-Kalem", encoding the FCV F9-Like and the VS-FCV capsid proteins respectively. The "pVHV" vector nomenclature was chosen to refer to pVEK-derived replicon vectors containing transgene cassettes cloned via the AscI and PacI sites in the multiple cloning site of pVEK.

To create the dual construct, the pVHV vector region encoding the VEE subgenomic promoter and FCV Kalem (VS-FCV) capsid sequences was removed by PCR and ligated into the pVHV-F9 vector between the 3' end of the F9 FCV capsid sequence and the VEE 3' UTR sequence. The duplication of the subgenomic promoter sequence and confirmation of the FCV Kalem capsid sequence were achieved by sequencing of the final vector clone, termed "pVHV-F9-Kalem".

Production of TC-83 RNA replicon particles (RP) was conducted according to methods previously described [U.S. Pat. No. 9,441,247 B2 and U.S. Pat. No. 8,460,913 B2; the contents of which are hereby incorporated herein by reference in their entireties]. Briefly, pVHV replicon vector DNA and helper DNA plasmids were linearized with NotI restriction enzyme prior to in vitro transcription using MegaScript T7 RNA polymerase and cap analog (Promega, Madison, Wis.). Importantly, the helper RNAs used in the production lack the VEE subgenomic promoter sequence, as previously described [Kamrud et al., *J Gen Virol.* 91(Pt 7):1723-1727 (2010)]. Purified RNA for the replicon and helper components were combined and mixed with a suspension of Vero cells, electroporated in 4 mm cuvettes, and returned to OptiPro® SFM cell culture media (Thermo Fisher, Waltham Mass.). Following overnight incubation, alphavirus RNA replicon particles were purified from the cells and media by passing the suspension through a ZetaPlus BioCap depth filter (3M, Maplewood, Minn.), washing with phosphate buffered saline containing 5% sucrose (w/v), and finally eluting the retained RP with 400 mM NaCl buffer. Eluted RP were formulated to a final 5% sucrose (w/v), passed through a 0.22 micron membrane filter, and dispensed into aliquots for storage. Titer of functional RP was determined by immunofluorescence assay on infected Vero cell monolayers.

Example 2

Evaluation of Efficacy and Safety of a Dual Construct FCV Vaccine in Cats

A dual-construct vaccine comprising a propagation defective RNA particle (RP) encoding the capsid proteins from two different strains of FCV, a virulent systemic strain (VS-FCV) and a classical vaccine strain (FCV F9-Like) along with the capsid protein and glycoproteins of the avirulent TC-83 strain of Venezuelan Equine Encephalitis Virus (VEE) was formulated in 5% sucrose and stored frozen. This dual-construct vaccine was used to evaluate the effectiveness against challenge by two FCV strains, as shown in Table 1 below. Two groups of 10 cats each were vaccinated with the dual-construct FCV vaccine in a prime/boost regimen at 13-14 weeks of age and then 21 days later. Two groups of control cats were vaccinated by the same regimen with a placebo vaccine consisting of cell culture media (Minimal Essential Media with Earle's salts, EMEM).

TABLE 1

VACCINATION PROTOCOL

| Treatment Group | No. of Animals | Test Product | Vaccine Dose | Challenge Strain |
|---|---|---|---|---|
| 1 | 9 | Dual-construct RP-FCV | $6.1 \times 10^7$ | Classical FCV (Strain 255) |
| 2 | 7 | Placebo | NA | Classical FCV (Strain 255) |
| 3 | 9 | Dual-construct RP-FCV | $6.1 \times 10^7$ | Virulent Systemic FCV (Kalem[#] strain) |
| 4 | 7 | Placebo | NA | Virulent Systemic FCV (Kalem strain) |

[#]Internal reference

Following the vaccinations the cats were observed for adverse reactions to the vaccines by observing the cats for any local or systemic reactions to the vaccines as well as clinical signs of FCV infection. No adverse reactions were observed for any of the vaccinated cats.

Three weeks following the booster vaccination, cats in Groups 1 and 2 were challenged intranasally with a virulent culture of FCV strain 255 (classical FCV challenge strain). Three weeks after booster vaccination cats in Groups 3 and 4 were challenged intranasally with a virulent culture of virulent systemic FCV challenge strain (FCV strain Kalem).

Cats were observed for clinical signs of FCV infection for 14 days following challenge as follows: cats were observed and scored daily for clinical signs including: death, depression/lethargy, body temperature, nasal and oral ulcers, nasal and ocular discharge, lameness, dehydration and sneezing. Body weight was measured on four days spaced throughout the 14 day post-challenge period. Each of the clinical signs observed was given a weighted numerical score based on severity and the number of days it was observed. Each cat was then given a total, weighted score based on the sum of the daily weighted scores. A mean and median weighted score was then calculated for each treatment group. For the challenge to be considered valid, 80% of the control cats must show clinical signs of FCV infection (other than fever). The results of the challenge are summarized in Table 2 below:

TABLE 2

CHALLENGE RESULTS

| Treatment Group | Test Product | Challenge Strain | Median Weighted Clinical Score | Mean Weighted Clinical Score |
|---|---|---|---|---|
| 1 | Dual-construct RP-FCV | Classical FCV (Strain 255) | 5 | 6.3 |
| 2 | Placebo | Classical FCV (Strain 255) | 16 | 14.3 |
| 3 | Dual-construct RP-FCV | Virulent Systemic FCV (Kalem strain) | 10 | 8.8 |
| 4 | Placebo | Virulent Systemic FCV (Kalem strain) | 38 | 36.9 |

The challenges for both strains were considered valid as 100% of placebo-vaccinated control cats exhibited clinical signs of FCV infection (other than fever). The dual-construct RP-FCV vaccine encoding a virulent systemic and classical vaccine strain of FCV protected cats against two distinct strains of FCV: a classical FCV strain as well as a virulent systemic FCV strain. The experimental vaccine was found safe in cats.

Example 3

Evaluation of Interference with Administration of Two Different RNA Particle Vaccines The study was conducted to evaluate multiple aspects of the alphavirus RNA replicon particle FCV vaccine including serological response, efficacy against challenge, and interference. A RP-FCV construct vaccine encoding the capsid protein of a classical FCV vaccine strain (F9) was formulated in stabilizer consisting of gelatin, NZ-amine, and sucrose and lyophilized. Two groups of five cats were vaccinated with the RP-FCV vaccine at 17 weeks of age. Twenty-one days later, cats in Group 1 were administered a booster dose of the RP-FCV vaccine only, cats in Group 2 were administered a booster dose of the RP-FCV vaccine and administered a dose of an RP-Rabies vaccine at the same time as shown in Table 3 below. The RP-Rabies virus vaccine is a construct encoding the rabies virus glycoprotein (G) in the same TC-83 VEE alphavirus platform.

TABLE 3

| VACCINATION PROTOCOL | | |
|---|---|---|
| Treatment Group | Test Product -Initial Vaccination (Day 0) | Test Product(s)-Booster Vaccination (Day 21) |
| 1 | RP-FCV (F9) | RP-FCV (F9) |
| 2 | RP-FCV (F9) | RP-FCV (F9) RP-Rabies virus |

Following each vaccination the cats were observed for adverse reactions to the vaccines by observing the cats for any local or systemic reactions to the vaccines. No adverse reactions were observed for any of the vaccinated cats.

Cats were bled for serum collection on the day of initial vaccination (Study Day 0), the day of booster vaccination (Study Day 21) and six weeks after the initial vaccination (Study Day 42). The serum was tested for antibody titer to FCV F9 by a serum neutralization assay. Serum was also tested for antibody titer to rabies virus by the Rapid Fluorescent Focus Inhibition Test (RFFIT). RIFFT results are reported as International Units per milliliter (IU/mL). Serology results are summarized in Tables 4 and 5 below.

TABLE 4

| FCV F9 SEROLOGY RESULTS | | | | |
|---|---|---|---|---|
| Treatment | Vaccination Regimen | FCV (F9) Antibody Titer (Geometric Mean) | | |
| Group | (Day 0/Day 21) | Day 0 | Day 21 | Day 42 |
| 1 | RP-FCV (F9)/ RP-FCV (F9) | <2 | 3 | 34 |
| 2 | RP-FCV (F9)/ RP-FCV (F9) + RP-Rabies virus | <2 | 3 | 38 |

Based on comparison of FCV (F9) antibody titers (on serum samples collected post-booster) concurrent vaccination with an RP-Rabies virus vaccine does not interfere with the antibody response to an RP-FCV (F9) vaccine.

TABLE 5

| RABIES VIRUS SEROLOGY RESULTS | | | | |
|---|---|---|---|---|
| Treatment | Vaccination Regimen | Rabies Antibody Titer (Geometric Mean IU/mL) | | |
| Group | (Day 0/Day 21) | Day 0 | Day 21 | Day 42 |
| 1 | RP-FCV (F9)/ RP-FCV (F9) | 2 | 1 | Not Tested |
| 2 | RP-FCV (F9)/ RP-FCV (F9) + RP-Rabies virus | 1 | <1 | 39 |

Although this study did not include a control group, which was vaccinated with only an RP-Rabies virus vaccine, for the purpose of comparing the post-booster rabies titer of Group 2, historical data from other studies is presented below in Table 6.

TABLE 6

| RABIES VIRUS SEROLOGY RESULTS, MULTIPLE STUDIES | | | | |
|---|---|---|---|---|
| | | | Rabies Antibody Titer (Geometric Mean IU/mL) | |
| Treatment Group | Vaccination Regimen | RP-Rabies virus Potency | Pre-vaccination | Approximately 1 month post-vaccination* |
| 2 | RP-FCV (F9)/ RP-FCV (F9) + RP-Rabies virus | $1.3 \times 10^7$ | 1 | 39 |
| Study RUS-006 | RP-Rabies virus alone Single Vaccination | $2.7 \times 10^7$ | <0.1 | 42.7 |
| Study RUS-006 | RP-Rabies virus alone Single Vaccination | $2.6 \times 10^6$ | <0.1 | 17.6 |

*Study RUS-006 cats were bled for serum 30 days after vaccination

Based on the potency of the RP-Rabies virus vaccines and the post-vaccination rabies antibody titers, a prior vaccination with an RP-FCV vaccine does not interfere with the antibody response to an RP-Rabies virus vaccine. Vector immunity is a concern with platform-based vaccines however, the results of this study suggest that multiple RP-based vaccines can be used in an animal without compromising efficacy.

In order to confirm the lack of interference by concurrent vaccination with RP-Rabies virus on RP-FCV (F9) efficacy the study was amended and continued. A group of five age-matched cats were added to the study to serve as non-vaccinated controls. All cats were challenged intranasally with a virulent, classical strain of FCV (FCV 255) 79 days after the initial vaccination of Groups 1 and 2.

For 14 days following challenge cats were observed and scored daily for the following clinical signs of FCV infection: death, depression/lethargy, body temperature, nasal and oral ulcers, nasal and ocular discharge, lameness, dehydration, and sneezing. Body weight was measured on four days spaced throughout the 14-day post-challenge period. Each of the clinical signs observed was given a weighted numerical score based on severity and the number of days it was observed. Each cat was then given a total, weighted score based on the sum of the daily weighted scores. A mean and median weighted score was then calculated for each treatment group. For the challenge to be considered valid, 80% of the control cats must show clinical signs of FCV infection (other than fever). The results of the challenge are summarized in the table below:

TABLE 7

| INTERFERENCE STUDY CHALLENGE RESULTS | | | |
|---|---|---|---|
| Treatment Group | Vaccination Regimen (Day 0/Day 21) | Mean Weighted Clinical Score | Median Weighted Clinical Score |
| 1 | RP-FCV (F9)/ RP-FCV (F9) | 3 | 4.0 |
| 2 | RP-FCV (F9)/ RP-FCV (F9) + RP-Rabies virus | 2 | 4.4 |
| 3 | Non-Vaccinated | 20 | 19.6 |

The challenge was considered valid as 100% of non-vaccinated control cats exhibited clinical signs of FCV infection (other than fever). Both vaccinate groups (Groups 1 and 2) were significantly protected from virulent FCV challenge (p values 0.012 for both groups).

Based on comparison of clinical scores, concurrent vaccination with an RP-Rabies virus vaccine does not interfere with the efficacy of an RP-FCV (F9) vaccine. The experimental vaccine was found safe in cats.

Example 4

Evaluation of Vaccine Efficacy in Cats of a RP Construct Encoding a Single FCV F9-Like Capsid Protein This study was conducted to further evaluate the efficacy of a feline vaccine comprising an alphavirus RNA replicon particle that encoded a single FCV F9-Like capsid protein (RP-FCV F9). The vaccine was compared to a placebo control group against a classical FCV challenge. Cats were inoculated with either this monovalent vaccine or a placebo and subsequently challenged with a classical FCV. The clinical scores are based on the typical signs of FCV infection, mainly oral and external ulcers and rhinitis, scored over a period of 14 days following the FCV challenge. The scoring system is the same as that described in Examples 2 and 3 above. Whereas, the mean clinical score for the placebo controls was 92, the mean clinical score for the RP-FCV F9 vaccine was only 2. Surprisingly the score for the RP-FCV F9 vaccine also was significantly lower than that obtained with two vaccines that individually comprised a single attenuated-live FCV F9-Like virus. This experiment further demonstrates that an RP-FCV vaccine encoding a classical vaccine strain of FCV protects cats against an FCV F9-Like virus.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

I claim:

1. An immunogenic composition comprising an alphavirus RNA replicon particle that encodes a feline calicivirus (FCV) antigen.

2. The immunogenic composition of claim 1, wherein the FCV antigen is a capsid protein or an antigenic fragment thereof.

3. The immunogenic composition of claim 2, wherein the alphavirus RNA replicon particle is a Venezuelan Equine Encephalitis (VEE) alphavirus RNA replicon particle.

4. The immunogenic composition of claim 3, wherein the capsid protein is selected from the group consisting of an FCV F9-Like capsid protein, an antigenic fragment of the FCV F9-Like capsid protein, a virulent systemic FCV (VS-FCV) capsid protein, and an antigenic fragment of the VS-FCV capsid protein.

5. The immunogenic composition of claim 4, wherein the capsid protein is a VS-FCV capsid protein or an antigenic fragment thereof.

6. The immunogenic composition of claim 5, that comprises an additional alphavirus RNA replicon particle that encodes an FCV F9-Like capsid protein or an antigenic fragment thereof.

7. The immunogenic composition of claim 5, wherein the alphavirus RNA replicon particle also encodes an FCV F9-Like capsid protein, or an antigenic fragment of the FCV F9-Like capsid protein.

8. The immunogenic composition of claim 5, wherein the VS-FCV capsid protein comprises an amino acid sequence comprising at least 95% identity with the amino acid sequence of SEQ ID NO: 2.

9. The immunogenic composition of claim 4, wherein the capsid protein is a FCV F9-Like capsid protein or an antigenic fragment thereof.

10. The immunogenic composition of claim 9, wherein the FCV F9-Like capsid protein comprises an amino acid sequence comprising at least 95% identity with the amino acid sequence of SEQ ID NO: 4.

11. A vaccine to aid in the prevention of disease due to FCV comprising the immunogenic composition of claim 4, and a pharmaceutically acceptable carrier.

12. The vaccine composition of claim 11, that further comprises at least one non-FCV antigen for eliciting protective immunity to a non-FCV feline pathogen.

13. The vaccine of claim 12, wherein the non-FCV feline pathogen is selected from the group consisting of feline herpesvirus (FHV), feline leukemia virus (FeLV), feline pneumovirus (FPN), feline parvovirus (FPV), feline infectious peritonitis virus (FIPV), feline immunodeficiency virus, borna disease virus (BDV), feline influenza virus, feline panleukopenia virus (FPLV), feline coronavirus (FCoV), feline rhinotracheitis virus (FVR), *Chlamydophila felis*, and any combination thereof.

14. The vaccine of claim 12, wherein the non-FCV antigen is an attenuated non-FCV antigen selected from the group consisting of feline herpesvirus (FHV), feline leukemia virus (FeLV), feline pneumovirus (FPN), feline parvovirus (FPV), feline infectious peritonitis virus (FIPV), feline immunodeficiency virus, borna disease virus (BDV), feline influenza virus, feline panleukopenia virus (FPLV), feline coronavirus (FCoV), feline rhinotracheitis virus (FVR), *Chlamydophila felis*, and any combination thereof.

15. The vaccine composition of claim 11, that further comprises an alphavirus RNA replicon particle comprising a nucleotide sequence encoding at least one protein antigen or an antigenic fragment thereof that originates from a non-FCV antigen; wherein the protein antigen or an antigenic fragment thereof that originates from a non-FCV feline pathogen selected from the group consisting of feline herpesvirus (FHV), feline leukemia virus (FeLV), feline pneumovirus (FPN), feline parvovirus (FPV), feline infectious peritonitis virus (FIPV), feline immunodeficiency virus, borna disease virus (BDV), feline influenza virus, feline panleukopenia virus (FPLV), feline coronavirus (FCoV), feline rhinotracheitis virus (FVR), *Chlamydophila felis*, and any combination thereof.

16. The vaccine composition of claim 11, that is a nonadjuvanted vaccine.

17. A method of immunizing a feline against a pathogenic FCV comprising administering to the feline an immunologically effective amount of the vaccine of claim 16.

18. The immunogenic composition of claim 1, that comprises an additional alphavirus RNA replicon particle that encodes a second FCV antigen, wherein the second FCV antigen originates from a different strain of FCV than the one from which the FCV antigen originates from.

19. The immunogenic composition of claim 18, wherein the additional alphavirus RNA replicon particle is an VEE alphavirus RNA replicon particle.

20. A vaccine to aid in the prevention of disease due to FCV comprising a Venezuelan Equine Encephalitis (VEE) alphavirus RNA replicon particle that encodes a feline calicivirus (FCV) F9-Like capsid protein comprising an amino acid sequence that comprises at least 95% identity with the amino acid sequence of SEQ ID NO: 4 and a VS-FCV capsid protein comprising an amino acid sequence that comprises at least 95% identity with the amino acid sequence of SEQ ID NO: 2.

* * * * *